United States Patent
Shah et al.

(10) Patent No.: US 10,024,780 B2
(45) Date of Patent: Jul. 17, 2018

(54) METHODS FOR DETECTING EVENTS IN A FLOW CYTOMETER

(71) Applicant: Abbott Laboratories, Abbott Park, IL (US)

(72) Inventors: Amish P. Shah, Pleasanton, CA (US); Frederic M. Hulett, III, Mountain View, CA (US)

(73) Assignee: Abbott Laboratories (Diagnostics Division), Abbott Park, IL (US)

( * ) Notice: Subject to any disclaimer, the term of this patent is extended or adjusted under 35 U.S.C. 154(b) by 0 days.

(21) Appl. No.: 15/379,846

(22) Filed: Dec. 15, 2016

(65) Prior Publication Data

US 2017/0176317 A1 Jun. 22, 2017

Related U.S. Application Data

(60) Provisional application No. 62/269,294, filed on Dec. 18, 2015.

(51) Int. Cl.
| | | |
|---|---|---|
| *G01N 15/14* | (2006.01) | |
| *G01N 21/64* | (2006.01) | |
| *G01N 21/15* | (2006.01) | |
| *G01N 21/05* | (2006.01) | |
| *G01N 15/00* | (2006.01) | |
| *G01N 15/10* | (2006.01) | |

(52) U.S. Cl.
CPC ....... *G01N 15/1429* (2013.01); *G01N 21/645* (2013.01); *G01N 21/6486* (2013.01); *G01N 21/05* (2013.01); *G01N 2015/0073* (2013.01); *G01N 2015/0084* (2013.01); *G01N 2015/1068* (2013.01); *G01N 2015/1402* (2013.01); *G01N 2015/1488* (2013.01); *G01N 2021/157* (2013.01)

(58) Field of Classification Search
CPC ............... G01N 15/14; G01N 15/1429; G01N 2015/0073; G01N 2015/0084; G01N 2015/1068; G01N 2015/1488; G01N 2015/1402; G01N 2015/1404; G01N 2015/1409; G01N 2015/1411; G01N 2015/149; G01N 2021/157; G01N 2021/6482; G01N 21/645; G01N 21/6486; G01N 2201/06113
USPC ............ 356/39–41, 311, 317, 318, 335–343, 356/432–444
See application file for complete search history.

(56) References Cited

U.S. PATENT DOCUMENTS

| | | | | |
|---|---|---|---|---|
| 5,030,002 A | * | 7/1991 | North, Jr. | G01N 15/1404 209/3.1 |
| 5,040,890 A | * | 8/1991 | North, Jr. | G01N 15/1404 356/72 |
| 5,631,165 A | | 5/1997 | Chupp et al. | |
| 5,760,900 A | * | 6/1998 | Ito | G01N 15/1434 250/461.2 |

(Continued)

*Primary Examiner* — Gordon J Stock, Jr.
(74) *Attorney, Agent, or Firm* — Edward J. Baba; Bozicevic Field & Francis LLP

(57) ABSTRACT

Aspects of the present disclosure include methods for detecting events in a flow cytometer. Also provided are methods of detecting cells in a flow cytometer. Other aspects of the present disclosure include methods for determining a level of contamination in a flow cell. Computer-readable media and systems, e.g., for practicing the methods summarized above, are also provided.

14 Claims, 19 Drawing Sheets

(56) References Cited

U.S. PATENT DOCUMENTS

| | | | |
|---|---|---|---|
| 8,045,162 B2* | 10/2011 | Vacca | G01N 15/0205 |
| | | | 356/337 |
| 9,329,117 B2* | 5/2016 | Yamaguchi | G01N 21/6408 |
| 9,677,990 B2* | 6/2017 | Pariseau | G01N 15/1459 |
| 9,709,769 B2* | 7/2017 | Rohani | G02B 7/022 |
| 2003/0048433 A1* | 3/2003 | Desjonqueres | G01N 21/53 |
| | | | 356/73 |
| 2009/0071225 A1* | 3/2009 | Schilffarth | G01N 15/1012 |
| | | | 73/1.02 |
| 2010/0203058 A1 | 8/2010 | Ingram et al. | |
| 2012/0309651 A1* | 12/2012 | Pregibon | C12Q 1/6816 |
| | | | 506/16 |
| 2014/0244217 A1 | 8/2014 | Lo et al. | |
| 2014/0268102 A1 | 9/2014 | Shah | |

* cited by examiner

METHODS FOR DETECTING EVENTS IN A FLOW CYTOMETER

CROSS-REFERENCE

This application claims the benefit of U.S. Provisional Patent Application No. 62/269,294 filed Dec. 18, 2015, which application is incorporated herein by reference in its entirety.

INTRODUCTION

A variety of methods are used for cellular analysis, including visual and/or automated inspection via light or fluorescent light microscopy. Cellular examinations and analyses of these types are commonly practiced in order to obtain information regarding cell lineage, maturational stage, and/or cell counts in a sample.

Flow cytometry is a method for identifying and distinguishing between different cell types in a non-homogeneous sample. In the flow cytometer, cells are passed one at a time or nearly one at a time through a sensing region where each cell is irradiated by an energy source. Typically, single wavelength light sources (e.g., lasers, etc.) are used as the energy source and one or more of a variety of sensors record data based on the interaction of the cells with the applied energy. Flow cytometry is commonly used in hematology and has been successful in the diagnosis of blood diseases, including blood cancers. In addition to flow cytometry, other analytical methods are used in hematology and in characterizing a population of cells.

Challenges in flow cytometry include the capture of noise-free particle events (e.g., cell events). For example, optical side-lobes, baseline drift, fluidics drift and/or the electronics baseline time constant produce undesirable signals that resemble small cell events. Other factors that adversely affect the quality of flow cytometry data include variation in nucleated cell counts from sample to sample, e.g., which results in variation in fluorescent signals such that the cell events occupy very little dynamic range of the analog to digital converter (ADC). In addition, flow cell contamination may prevent a flow cytometer from producing valid clinical results.

SUMMARY

Aspects of the present disclosure include methods for detecting events in a flow cytometer. Such methods include flowing particles through a flow cell of a flow cytometer, optically interrogating the particles flowing through the flow cell, extracting putative event features, and time-stamping putative events. Such methods further include determining a time difference between a putative previous event and a putative current event and comparing the time difference to a threshold duration. If the time difference is greater than the threshold duration, the putative current event is stored as a current event. If the time difference is less than the threshold duration, a peak height feature of the putative current event and a peak height feature of the putative previous event are compared to a threshold peak height. If the peak height feature of the putative current event is less than the threshold peak height, the putative current event is discarded. If the peak height feature of the putative previous event is less than the threshold peak height, the putative previous event is discarded. If the peak height feature of the putative previous event is greater than the threshold peak height, the putative previous event is stored as a previous event.

Also provided are methods of detecting cells in a flow cytometer. Such methods include flowing a cellular sample through a flow cell of a flow cytometer, detecting optical signals from the cells flowing through the flow cell at a first gain setting, and detecting optical signals from the cells flowing through the flow cell at the second gain setting. The second gain setting is different from the first gain setting.

Other aspects of the present disclosure include methods for determining a level of contamination in a flow cell. Such methods include flowing a sample including particles through a flow cell, collecting raw particle event data during the flowing, counting the number of particle events within the raw particle event data and filtering the raw particle event data with an inverse Gaussian filter coefficient to produce a filtered signal. The inverse Gaussian filter coefficient is based on an expected power spectrum variance. Such methods further include determining the energy of the filtered signal, and subtracting a clean flow cell baseline energy from the determined energy of the filtered signal, to determine a level of contamination in the flow cell.

Computer-readable media and systems, e.g., for practicing the methods of the present disclosure, are also provided.

DETAILED DESCRIPTION

Figure 1:
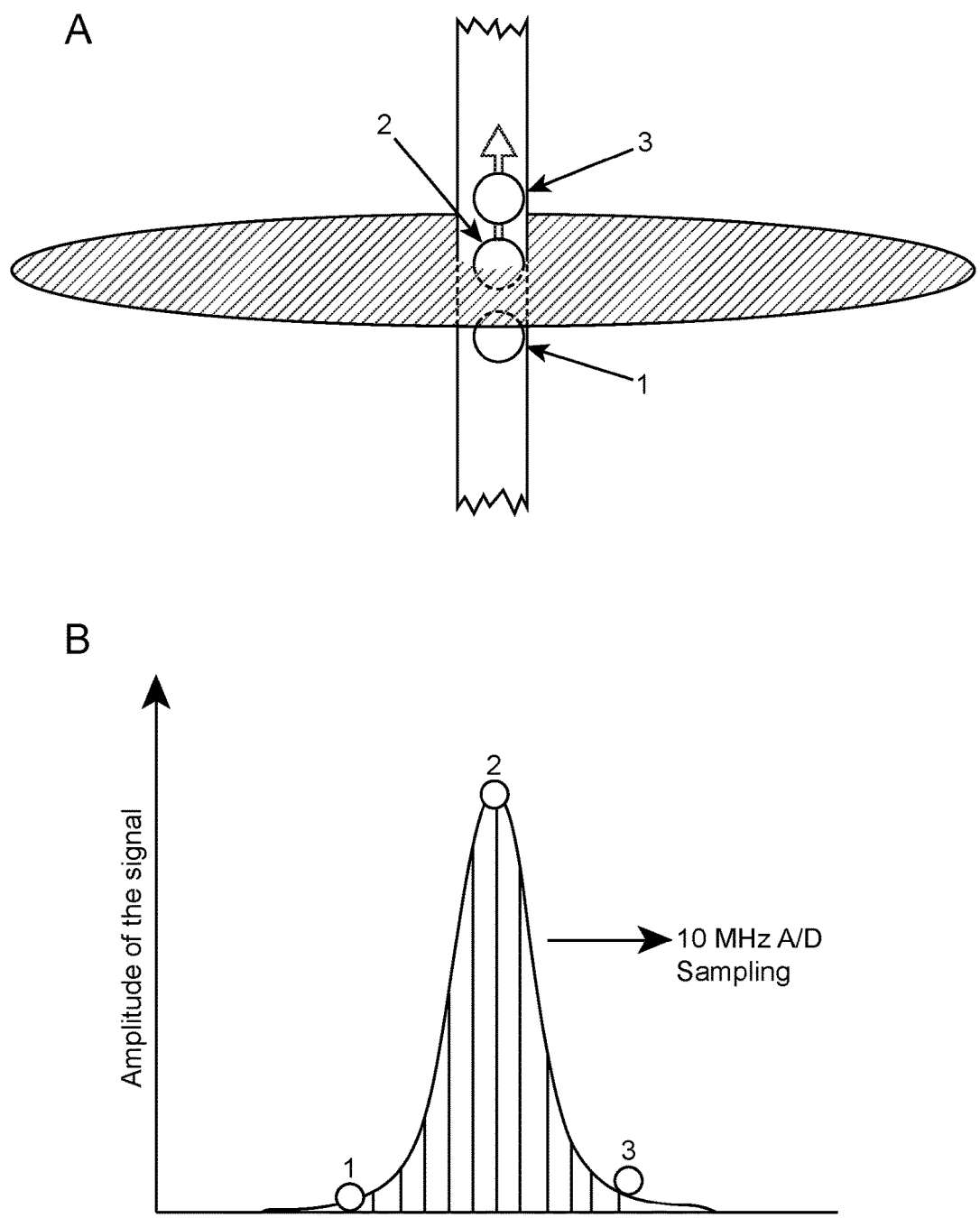
FIG. 1, panels A and B, depict how a cell particle travels within an illuminated flow cell and the plotted convolution response, respectively.

Aspects of the present disclosure include methods for detecting events in a flow cytometer. Also provided are methods of detecting cells in a flow cytometer. Other aspects of the present disclosure include methods for determining a level of contamination in a flow cell. Computer-readable media and systems, e.g., for practicing the methods summarized above, are also provided.

Before the present methods, computer-readable media, and systems are described in greater detail, it is to be understood that the present disclosure is not limited to particular embodiments described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the present methods, computer-readable media, and systems. The upper and lower limits of these smaller ranges may independently be included in the smaller ranges and are also encompassed within the methods, computer-readable media, and systems, subject to any specifically excluded limit in the stated range. Where the stated range includes one or both of the limits, ranges excluding either or both of those included limits are also included in the methods, computer-readable media, and systems.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present invention, representative illustrative methods, computer-readable media, and systems are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods, computer-readable media, and systems. Any recited method can be carried out in the order of events recited or in any other order which is logically possible.

Methods

As summarized above, aspects of the present disclosure include methods for detecting events in a flow cytometer. Capturing noise-free cell events is made difficult by phenomena such as optical side-lobes, fluidics drift, baseline drift, flow cell contamination, and the like. These phenomena produce undesirable signals that resemble small cell events. These undesirable signals are often generated before and/or after a larger valid signal has been generated. These erroneously captured undesirable signals contaminate the feature extraction of valid cell events, e.g., small cell events.

Cell particles travel within an illuminated flow cell as depicted in FIG. 1, Panel A. During the time a cell particle travels within the illuminated volume (as shown at positions 1, 2 and 3), a photo detector captures the response of the convolution of the laser beam profile and cell particle. The convolution response is shown in FIG. 1, Panel B.

$$CellEvent(t) \equiv CellParticle(t) * laserprofile(t) = \int_0^t CellParticle(t) laserprofile(t-\tau)dt$$

A digital data capture system can digitize this cell event response, e.g., at a rate of 20 mega samples per second. The width of the cell event response depends on the velocity of the stream and height of the laser beam profile. This cell event response generates an approximately Gaussian waveform which can be characterized as:

$$CellEvent(t) = \frac{1}{\sigma\sqrt{2\pi}} e^{\frac{-(t-u)^2}{2\sigma^2}}$$

The parameter μ is a mean of the standard distribution and σ is the standard deviation (while the normal statistical distribution, characterized by a mean and standard deviation, is Gaussian in nature, the Gaussian signal pulse is not statistical). The variance ($\sigma^2$) of this distribution depends on the stream velocity in the flow cell. As long as the sheath pressure (and hence the stream velocity) is nearly constant in the flow cell, pulse width (duration at 1/e2 points) of the distribution is nearly constant.

During hematology analysis, platelets (PLT) are the smallest types of the cells to detect in the presence of larger reticulocytes and white blood cells. In order to accurately count platelets, the platelets must be distinguished from undesired noise-like cell events. Optical side-lobes, fluidics baseline drift, and the like produce undesirable signals which resemble valid cell event responses. The time proximity of the larger cell event negatively affects the valid small cell (e.g., platelet) event histogram. The present inventors have found that the addition of a high resolution time-stamp—added while extracting features of every cell event—may be exploited to detect and remove the artifacts generated by optical side-lobes, fluidics baseline drift, and the like. The inventors have found that it is possible to isolate small amplitude events in the proximity of the larger cell events by employing a high resolution time-stamp for each extracted cell event. Feature extraction according to the methods of the present disclosure enables determination from the pulse width whether proximity events are valid cell (e.g., platelet) events or signals derived from optical system side-lobes, fluidics drift, baseline drift, flow cell contamination, and/or the like.

According to certain embodiments, the methods for detecting events in a flow cytometer include flowing particles through a flow cell of the flow cytometer, optically interrogating the particles flowing through the flow cell, extracting putative event features, and time-stamping putative events. Such methods further include determining a time difference between a putative previous event and a putative current event and comparing the time difference to a threshold duration. If the time difference is greater than the threshold duration, the putative current event is stored as a current event. If the time difference is less than the threshold duration, a peak height feature of the putative current event and a peak height feature of the putative previous event are compared to a threshold peak height. If the peak height feature of the putative current event is less than the threshold peak height, the putative current event is discarded. If the peak height feature of the putative previous event is less than the threshold peak height, the putative previous event is discarded. If the peak height feature of the putative previous event is greater than the threshold peak height, the putative previous event is stored as a previous event.

By "event" is meant the passing of a particle (e.g., a cell) through an interrogation zone of the flow cell, as detected by an optical interrogation system. By "putative event" is meant optical signal features resembling an event which may or may not be produced by an event. The methods of the present disclosure enable the determination of whether a putative event is indeed an event, or whether the putative event is derived from signals which resemble valid cell event responses but are not in fact valid cell event responses, e.g., signals arising from optical side-lobes, fluidics baseline drift, and the like. As such, in certain aspects of the subject methods, an event is distinguished from a signal selected from optical system side-lobes, fluidics drift, baseline drift, flow cell contamination, and combinations thereof.

Flow stream velocity is a function of sheath pressure, fluid viscosity and flow cell dimensions. In certain aspects, flowing cells through the flow cell includes flowing the cells at a sheath pressure of 9 psi or greater, e.g., 9 psi, 10 psi or greater, 11 psi or greater, 12 psi or greater, 13 psi or greater, 14 psi or greater, 15 psi or greater, etc. According to certain embodiments, the beam height of the laser is 5 μm or greater, e.g., 5 μm, 6 μm or greater, 7 μm or greater, 8 μm or greater, 9 μm or greater, 10 μm or greater, 15 μm or greater, or 20 μm or greater.

Figure 2:
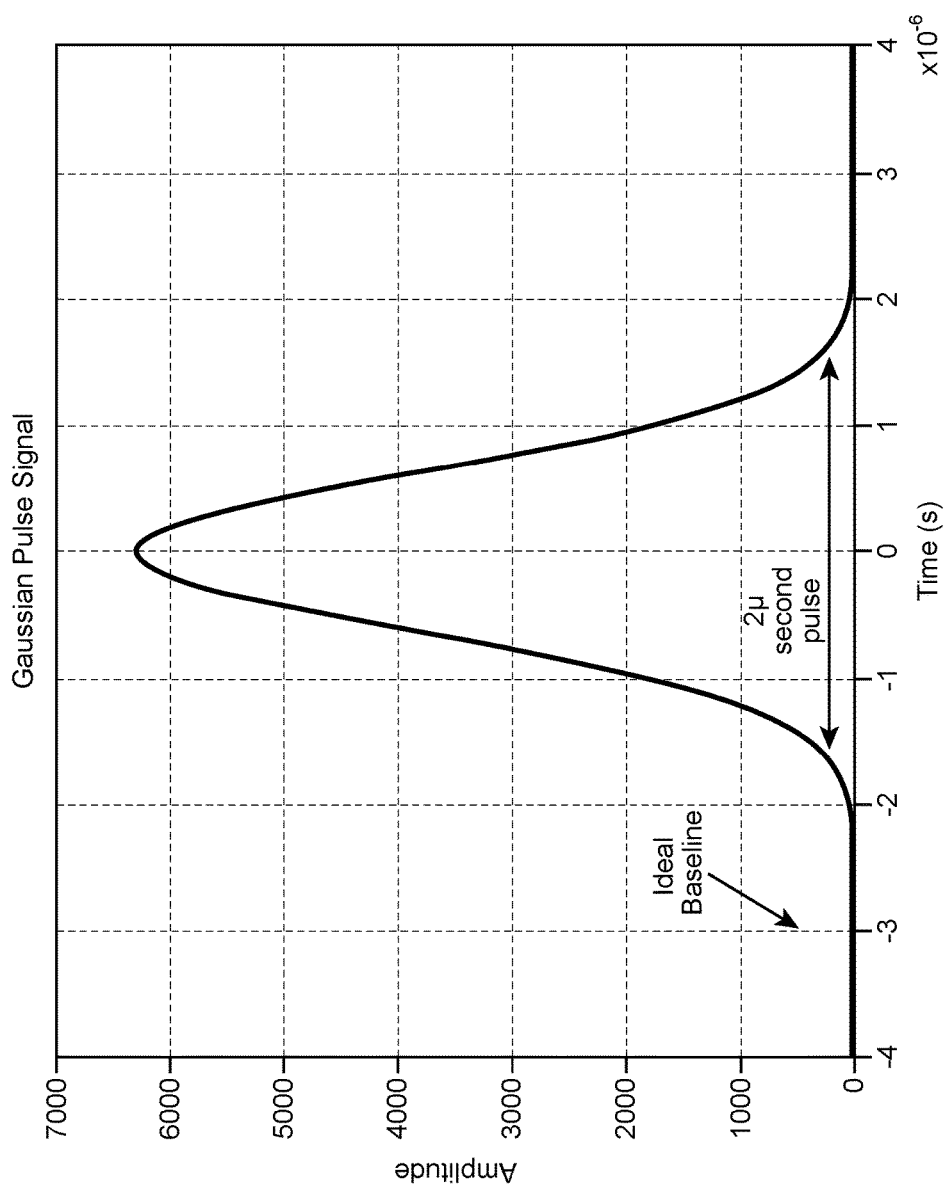
FIG. 2 depicts a plot showing an ideal "clean" Gaussian response.
Figure 3:
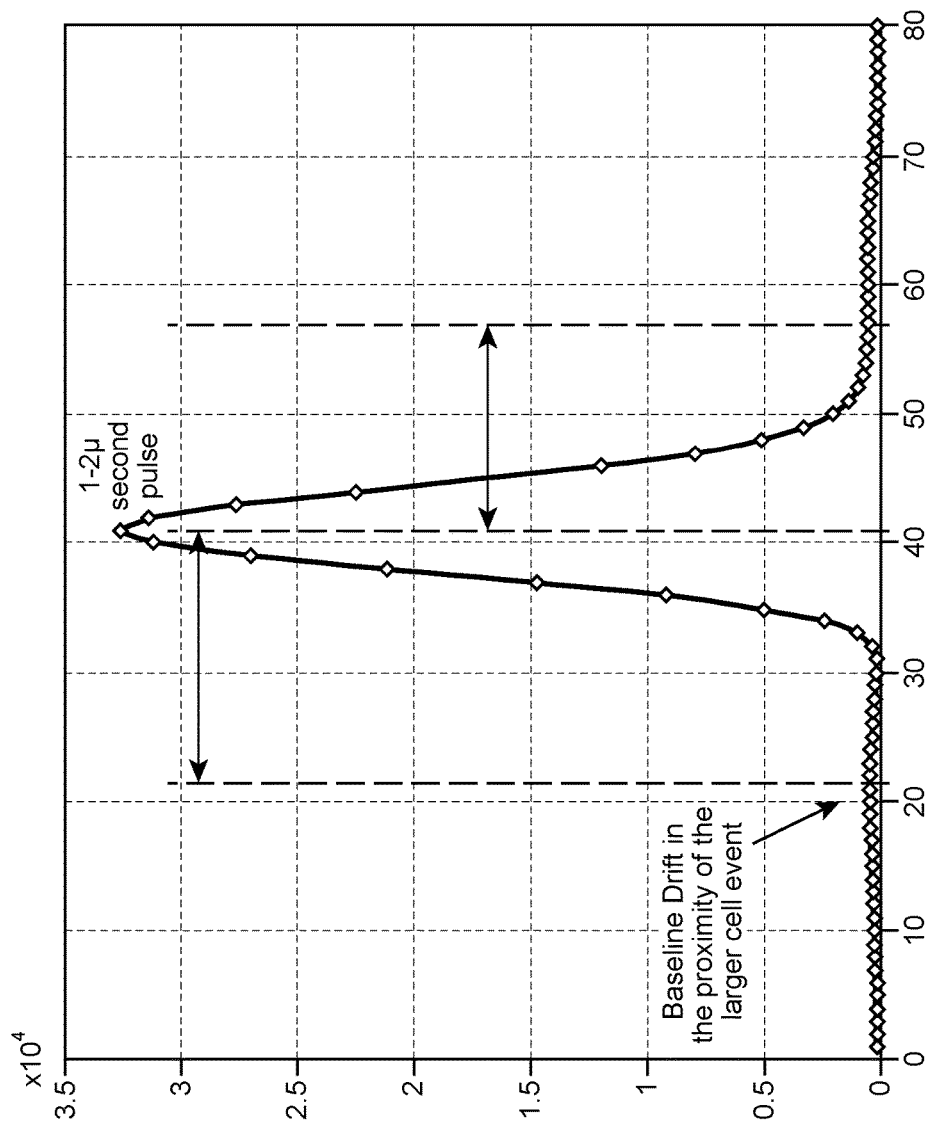
FIG. 3 depicts a plot showing baseline drift and undesirable cell event response.

Particles (e.g., cells) convolve with laser beam height to generate event profiles. When the sheath pressure is about 12 psi and the laser beam height is about 8 μm, this event profile divided by flow-stream velocity produces approximately 2 μs wide Gaussian pulses. An ideal ("clean") Gaussian response is depicted in FIG. 2. Under ideal conditions, there are no undesirable signals near the main Gaussian particle profile. However, in practice, phenomena such as optical side lobes, fluidics drift, baseline drift, and the like, produce undesirable signals near the main Gaussian particle profile. As an example, FIG. 3 shows a signal near the main Gaussian particle profile arising from baseline drift. The present inventors have found that, by processing the particle feature extraction according to the methods of the present disclosure, it is possible to determine whether a putative event is an event (e.g., the passing of a cell (e.g., a platelet) through the flow cell) or a non-event.

According to certain embodiments, the threshold duration is 2.5 μs or less, e.g., 2 μs. In certain aspects, comparing a peak height feature of the putative current particle event and a peak height feature of the putative previous particle event to a threshold peak height includes determining whether the peak heights of the putative current cell event and putative previous cell event are less than 2× a threshold peak height.

In certain aspects, the particles are microparticles, such as microparticles having fluorescent moieties incorporated therein, or having fluorescent moieties attached directly or indirectly to the surface thereof. By "microparticle" is meant a particle (which is not a cell), having a greatest dimension ranging from 0.001 μm to 1000 μm, such as from 0.5 μm to 100 μm, e.g., 0.1 μm to 20 μm. In certain aspects, the microparticle has a greatest dimension of 20 μm or less, such as 15 μm or less, 10 μm or less, 5 μm or less, 1 μm or less, 0.75 μm or less, 0.5 μm or less, 0.4 μm or less, 0.3 μm or less, 0.2 μm or less, 0.1 μm or less, 0.01 μm or less, or 0.001 μm or less.

The microparticles may have any suitable shape, including but not limited to spherical, spheroid, rod-shaped, disk-shaped, pyramid-shaped, cube-shaped, cylinder-shaped, nanohelical-shaped, nanospring-shaped, nanoring-shaped, arrow-shaped, teardrop-shaped, tetrapod-shaped, prism-shaped, or any other suitable geometric or non-geometric shape.

The microparticles may be made of any suitable material, including but not limited to, latex, polystyrene, silica, a magnetic material, a paramagnetic material, or any combination thereof.

According to certain embodiments, the particles are cells and an event is a cell event. The cells may be present in a cellular sample of interest, including but not limited to a blood sample (e.g., a whole blood sample or fraction thereof), a cerebrospinal fluid sample, a peritoneal fluid sample, a pericardial fluid sample, a pleural fluid sample, a synovial fluid sample, a urine sample, a saliva sample, a tear sample, a semen sample, an amniotic fluid sample, a sputum sample, and the like, as well as samples obtained from cysts, tumors, and the like. According to certain embodiments, a cell event is a small cell event. For example, the cell event may be a platelet event, e.g., in the vicinity of a Gaussian profile of a larger cell event, such as a Gaussian profile of a white blood cell (WBC) event. Other small cell events which may be determined by the methods of the present disclosure include microorganism cell events. Microorganisms of interest include bacteria, archaea, protozoa, fungi, algae and the like. According to certain embodiments, the small cell event is a cell debris event.

An example method for detecting events in a flow cytometer, and its utility in obtaining clean event histograms for events such as platelet events, is provided in Example 1 of the Experimental section below.

As summarized above, the present disclosure also provides methods for detecting cells in a flow cytometer. Such methods include flowing a cellular sample including cells through a flow cell of a flow cytometer, detecting optical signals from the cells flowing through the flow cell at a first gain setting, and detecting optical signals from the cells flowing through the flow cell at the second gain setting. The second gain setting is different from the first gain setting.

The methods employing first and second gain settings find a variety of uses. For example, the present inventors have found that changing the gain of the photo electronics signals during a flow cytometric assay makes it possible to use the entire dynamic range of the analog to digital converter (ADC). This improves the signal to noise ratio (SNR) and resolution from analog to digital conversion. Optimum gain settings of the photo electronic signals can be employed to increase the distance metrics in the clusters and provide better differentiation.

A first particular useful example application of the present methods that employ at least first and second gain settings is for detecting cells in cellular samples (e.g., body fluid samples) that exhibit substantial variation (e.g., from 5 to 5 million) in cell counts from sample to sample. A fixed amount of fluorescent dye is typically added in the assay prior to injecting the cellular sample in the flow stream. This fixed amount is selected based on the median expected cell events in the sample. If the sample has greater than normal nucleated cells, the dye concentration may not be sufficient to stain the higher number of cells. The resulting weak staining produces sub-optimal fluorescent signal and the cell events signals occupy only a small portion of the dynamic range of the ADC. By changing the gain settings (e.g., the gain settings of the photo diodes and/or photomultiplier tube) after the initial data capture, it is possible to set the gains such that all photo sensor signals occupy the full dynamic rage of the ADC. With this full ADC resolution, the present inventors have found that it is easier to differentiate between various cell types.

During the initial data period of data capture, photo sensor signals may be collected with default gain settings. An optimal gain setting to effectively use the complete dynamic range of the ADC may be computed within few milliseconds. The revised gain settings may be applied for the remaining duration of the assay, providing better signal to noise ratio and full use of dynamic range of the ADC. An example method that employs first and second gain settings is provided in Example 2 of the Experimental section below.

Figure 9:
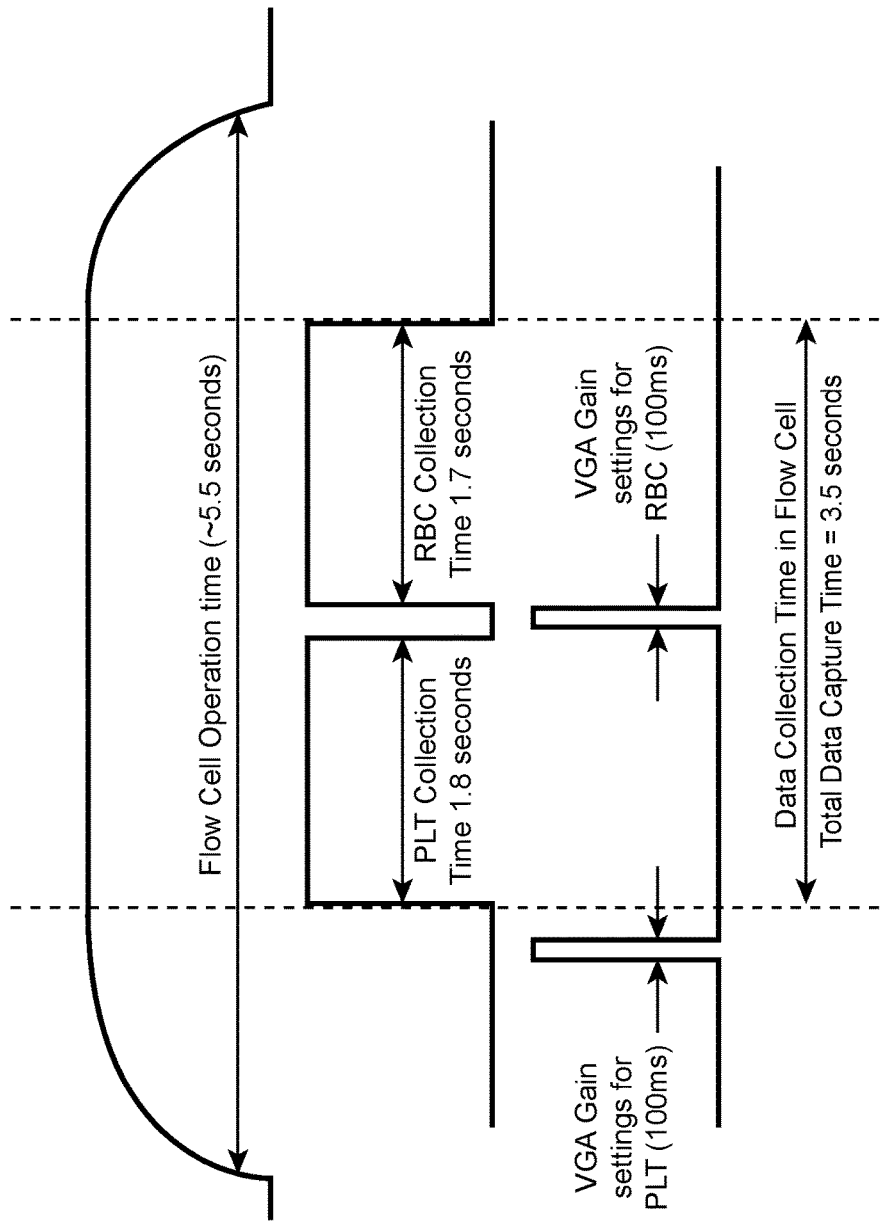
FIG. 9 depicts switching from a PLT collection gain setting to an RBC collection gain setting during the course of a single assay.

A second particular useful example application of the present methods that employ at least first and second gain settings is for counting different types of cells in a heterogeneous cellular sample (e.g., a blood sample) where the different cell types produce flow cytometric signals of different intensity. By way of example, the methods find use in capturing platelet events at a first (lower) gain setting, and capturing red blood cell (RBC) events at a second (higher) gain setting, as schematically illustrated in FIG. 9. In the example embodiment shown in FIG. 9, PLT collection occurs for a duration (1.8 seconds in this example) at a first gain setting, and then RBC collection subsequently occurs for a duration (1.7 seconds in this example) at a second gain setting. In this way, the assay can be performed in a first "mode" (e.g., a PLT mode) and then switched to a second "mode" (e.g., an RBC mode) in which the first and second modes differ according to the gain settings. A PLT mode may be run to capture details of PLT cell events, such as low end of PLT concentration, platelet distribution width (PDW) and/or mean platelet volume (MPV). Once the PLT data is captured, the gain settings are optimally lowered for collection of RBC cell events such that RBC cells occupy the full dynamic range of the ADC. While the RBC data is being captured, the PLT concentration and cell count result is available. When the blood sample exhibits a very low end of PLT count, the gain settings may be set back (increased) to capture more PLT cell events as may be necessary for statistical relevance.

Accordingly, aspects of the methods that employ at least first and second gain settings include analyzing the optical signals detected at the first gain setting to detect a first cell type, and analyzing the optical signals detected at the second gain setting to detect a second cell type.

When practicing the present methods employing first and second gain settings, the second gain setting may be greater than the first gain setting, e.g., when it is determined that the cell event signal strength is less than optimal (e.g., to account for a cellular sample having a higher than normal cell concentration). In certain aspects, the second gain setting may be less than the first gain setting, e.g., when it is determined that the cell event signal strength is greater than optimal (e.g., to account for a cellular sample having a lower than normal cell concentration).

According to certain embodiments, the first and second gain settings independently include a photo diodes gain setting, a photo multiplier tubes (PMT) gain setting, or both.

It will be understood that while the methods include first and second gain settings, the methods may employ a plurality of gain settings as may be desired for optimal collection of various cell events (e.g., corresponding to various cell types, etc.). For example, 2 or more, 3 or more, 4 or more, 5 or more, 6 or more, 7 or more, 8 or more, 9 or more, or 10 or more different gain settings may be employed during an assay for optimal collection of various cell events.

The detection of optical signals at the first gain setting may be for the same duration as detection of optical signals at the second gain setting. In other aspects, detecting optical signals at the first gain setting is for a different duration than detecting optical signals at the second gain setting. According to certain embodiments, detecting optical signals at the first and second gain settings is for a duration independently selected from 0.1 to 10 seconds (e.g., 0.5 to 5 seconds).

In certain aspects, a flow cytometric assay is run for an initial duration at the first gain setting, and then run for the remaining duration (which may be longer than the initial duration) of the assay at an improved (e.g., optimal) second gain setting. The improved gain setting may be determined based on signals (e.g., signal strength) collected during the initial duration at the first gain setting.

As summarized above, the present disclosure also provides methods for determining a level of contamination in a flow cell. By "contamination in a flow cell" or "flow cell contamination" is meant deposits (e.g., of cellular debris, protein, and/or the like) on the inside wall of the flow cell.

When these deposits occur, the optical path through the flowcell becomes clouded, distorting the laser beam and changing the intensity of the various scattered/fluorescent light signals.

Such methods include flowing a sample including particles through a flow cell, collecting raw particle event data during the flowing, and counting the number of particle events within the raw particle event data. The methods further include filtering the raw particle event data with an inverse Gaussian filter coefficient to produce a filtered signal, where the inverse Gaussian filter coefficient is based on an expected power spectrum variance. The methods further include determining the energy of the filtered signal (which is proportional to the contamination in the flowcell and number of cell events in the raw particle event data), and subtracting a clean flow cell baseline energy from the determined energy of the filtered signal, to determine a level of contamination in the flow cell. According to certain embodiments, subsequent to collecting raw particle event data during the flowing, the raw data values below threshold are replaced with zero. In certain aspects, the value resulting from subtracting the clean flow cell baseline energy from the determined energy of the filtered signal is scaled based on the number of events.

The methods find use in determining a level of contamination in a flow cell. According to certain embodiments, an application of the methods is to detect an early stage of flow cell contamination. A feature of the methods is that they permit detection of flow cell contamination such that the need to run a standard (e.g., a standard reference particle (SRP)) in a flow cytometer to detect flow cell contamination is obviated.

A contaminated flow cell generates more than one reflection and therefore smears, overlaps with, and adds distortion to a particle (e.g., cell) event response. The added signal arising from flow cell contamination distorts the original signal and generates a higher frequency component within the cell event spectrum. The present inventors have found that early stages of flow cell contamination may be detected by analyzing the particle event response in the frequency domain and assessing the energy of the high frequency component.

Referring to the formula above characterizing the Gaussian waveform generated by a cell event response, parameter p depends upon the baseline fluctuations. Baseline fluctuations may originate from external interference, laser noise, dark current and/or imperfections in the system electronics. A baseline restore (BLR) circuit maintains the baseline at DC. Parameter p may be brought to zero by eliminating the DC offset either by an analog BLR circuit or subtracting DC offset in the digital domain. Because parameter p can be brought to zero and variance is constant for the time-domain distribution for all the particle events, it is possible to transform this time-domain signal to the constant frequency domain spectrum. The frequency domain characteristic of the signal shows the same spectrum for all cell size-related cell events. It is therefore possible to exploit this characteristic to avoid running standard reference particles (SRP).

Accurate determination of a change in energy of the high frequency spectrum due to flow cell contamination is facilitated by removal of the energy in the spectrum accumulated from the clean flow-cell. According to the present methods, the inverse Gaussian Filter or High Pass Frequency Filter is computed, thereby inversing the power spectrum for the clean flow cell event. Since the complete waveform may be captured at high resolution (e.g., 16-bit and 10 MSPS), it is viable to digitally filter out the energy that is Gaussian in nature. Either finite impulse response (FIR) or infinite impulse response (IIR) filters in analog or digital form can be implemented to filter out this energy.

According to certain embodiments, a digital FIR filter is employed to remove the energy contributed from the clean flow-cell. FIR filter implementation may be carried out according to the following equation:

$$y[n]=b_0x[n]+b_1x[n-1]+ \ldots +b_Nx[n-N]$$

The equation for FIR filter implementation in the digital domain has $b_0 \; b_1 \; b_2 \; b_3 \ldots b_n$ coefficients which are computed from the inverse of the spectrum, and x(n) is the Digitized Raw Data Signal. Y(n) is the Digital output signal of the filter. The coefficients ($b_0 \; b_1 \; b_2 \; b_3 \ldots b_n$) can be modified further to remove the exact energy contributed by the clean cell event.

By removing the normal (clean) energy from the signal, the extra energy of multiple reflections and distortion of the signal may be computed. The energy measurement of the high frequency component indicates the order of contamination in the flow cell.

According to certain embodiments, counting the number of particle events includes extracting raw data of a fixed time interval from an analog to digital converter, determining a DC offset, and replacing the raw data that is below a fixed threshold with zeroes. In certain aspects, the threshold is from 1% to 5% of full dynamic range, or the threshold is 1/e2 of peak amplitude.

In certain aspects, the sample is flowed into a stream of sheath fluid within the flow cell, and the expected power spectrum variance is based on the pressure of the sheath fluid. According to certain embodiments, the particles are cells. For example, the sample may be a blood sample, and the particles are blood cells.

Figure 12:
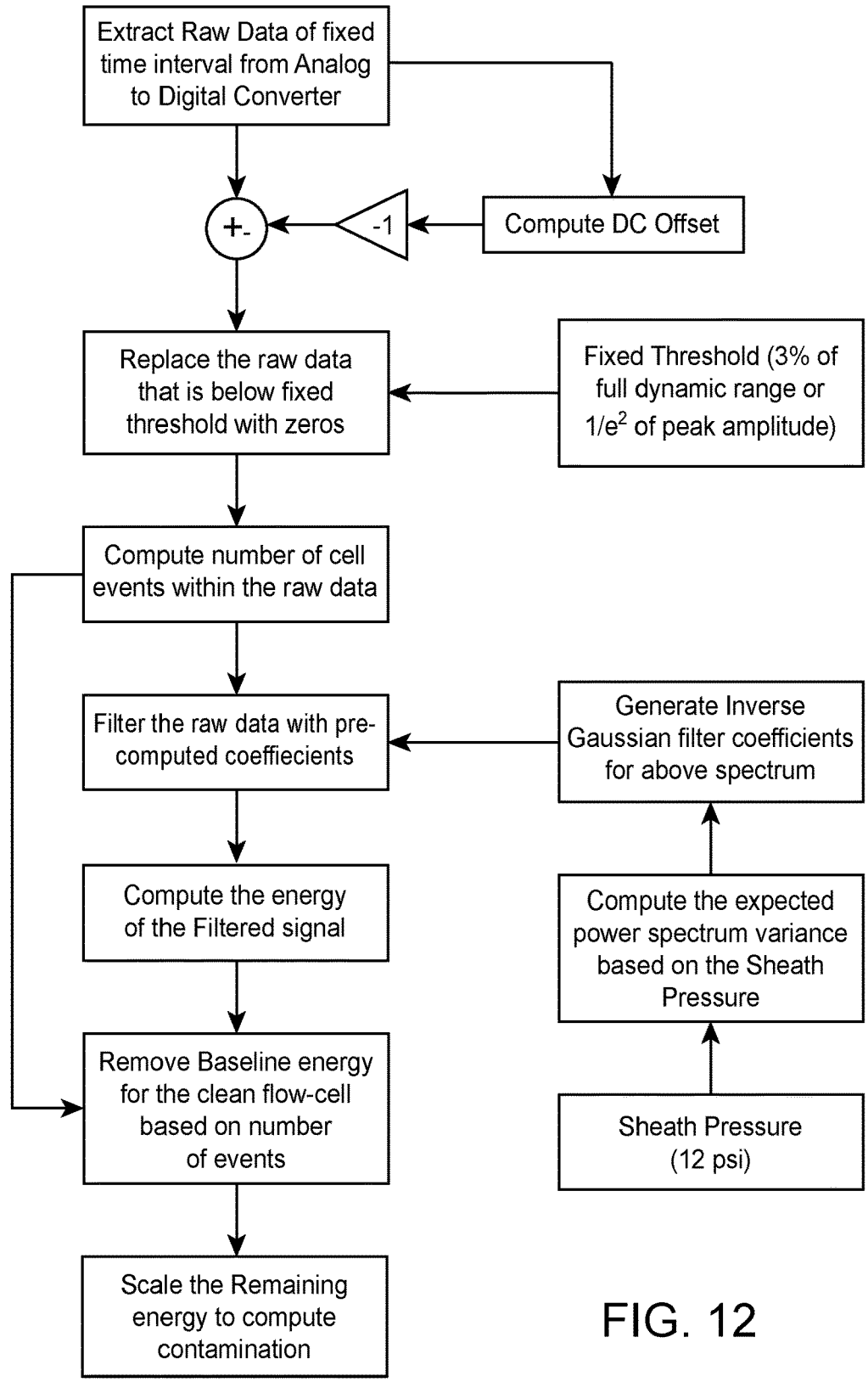
FIG. 12 is a flow chart for determining a level of contamination in a flow cell according to one embodiment of the present disclosure.

A flow chart of a method for determining a level of contamination in a flow cell according to one embodiment of the present disclosure is provided in FIG. 12. In this example, raw data of a fixed time interval is extracted from the analog to digital converter (ADC). A DC offset is computed. The raw data below a fixed threshold (e.g., 3% of full dynamic range or 1/e2 of peak amplitude) is replaced with zeroes. The number of cell events with the raw data is computed. The raw data is then filtered with pre-determined coefficients, and then the energy of the filtered signal is computed. Baseline energy for a clean flow cell is removed based on the number of cell events. The remaining energy may be scaled to determine the level of contamination.

An example method for determining a level of contamination in a flow cell is described in Example 3 of the Experimental section below.

When the flow cell starts becoming contaminated, feature calculations (e.g., peak height, width and higher moments) of cell events start to become invalid, which in turn produces erroneous reports, e.g., blood reports. According to existing methods, it is not possible to detect erroneous blood results until the flow cell is cleaned at scheduled intervals or a diagnostic mode involving standard reference particles (SRPs) is run. The methods of the present disclosure make it possible to detect the early stage of flow cell contamination, thereby enabling the avoidance of erroneous blood results and obviating the need for operating the flow cytometer in a special mode involving expensive SRP beads. In addition, discarded samples are minimized on account of the methods enabling detection of very early stages of flow cell contamination. Further, the system does not need to be cleaned (e.g., bleached) more frequently than required, thereby increasing the life of the tubing in the system.

Computer-Readable Media and Systems

As summarized above, also provided by the present disclosure are computer-readable media and systems, e.g., which find use in practicing the methods of the present disclosure.

Non-transitory computer readable media of the present disclosure include, but are not limited to, disks (e.g., magnetic or optical disks), solid-state storage drives, cards, tapes, drums, punched cards, barcodes, and magnetic ink characters and other medium that may be used for storing representations, instructions, and/or the like.

In certain aspects, provided are non-transitory computer-readable media that find use in practicing the methods for detecting events in a flow cytometer described hereinabove. According to certain embodiments, such non-transitory computer-readable media include instructions that, when executed by a computing device (e.g., a computing device of a flow cytometer), cause the computing device to extract putative event features from particles flowing through a flow cell, time-stamp putative events, determine a time difference between a putative previous event and a putative current event, and compare the time difference to a threshold duration. If the time difference is greater than the threshold duration, the instructions cause the computing device to store the putative current event as a current event. If the time difference is less than the threshold duration, the instructions cause the computing device to compare a peak height feature of the putative current event and a peak height feature of the putative previous event to a threshold peak height. If the peak height feature of the putative current event is less than the threshold peak height, the instructions cause the computing device to discard the putative current event. If the peak height feature of the putative previous event is less than the threshold peak height, the instructions cause the computing device to discard the putative previous event. If the peak height feature of the putative previous event is greater than the threshold peak height, the instructions cause the computing device to store the putative previous event as a previous event. In certain aspects, an event is distinguished from a signal selected from optical system side-lobes, fluidics drift, baseline drift, flow cell contamination, and combinations thereof. According to certain embodiments, the particles are cells, such that an event is a cell event. Cell events of interest include, e.g., small cell events. Small cell events may be platelet events, a microorganism cell event, a cell debris event, and/or the like.

In certain aspects, provided are non-transitory computer-readable media that find use in practicing the above-described methods for detecting cells in a flow cytometer. According to certain embodiments, such non-transitory computer-readable media include instructions that, when executed by a computing device (e.g., a computing device of a flow cytometer), cause the computing device to detect optical signals from cells of a cellular sample flowing through a flow cell at a first gain setting, change the gain setting from the first gain setting to a second gain setting, and detect optical signals from cells flowing through the flow cell at the second gain setting. The second gain setting is different from the first gain setting. For example, the second gain setting may be greater than the first gain setting (e.g., to account for the cellular sample having a high cell concentration, or to detect cell types that typically exhibit a weaker signal intensity). In other aspects, the second gain setting is less than the first gain setting (e.g., to account for the cellular sample having a low cell concentration, or to detect cell types that typically exhibit a strong signal intensity). The first and second gain settings may include a photo diodes gain setting, a photo multiplier tubes (PMT) gain setting, or both. According to certain embodiments, the first gain setting is higher than the second gain setting, and platelets are detected at the first gain setting and red blood cells (RBCs) are detected at the second gain setting. Detecting optical signals at the first gain setting may be for the same or a different duration as detecting optical signals at the second gain setting. In certain aspects, detecting optical signals at the first and second gain settings is for a duration independently selected from 0.1 to 10 seconds (e.g., 0.5 to 5 seconds).

In certain aspects, provided are non-transitory computer-readable media that find use in practicing the above-described methods for determining a level of contamination in a flow cell. According to certain embodiments, such non-transitory computer-readable media include instructions that, when executed by a computing device (e.g., a computing device of a flow cytometer), cause the computing device to collect raw particle event data as a sample including particles is flowed through a flow cell, count the number of particle events within the raw particle event data, and filter the raw particle event data with an inverse Gaussian filter coefficient to produce a filtered signal. The inverse Gaussian filter coefficient is based on an expected power spectrum variance. The instructions further cause the computing device to determine the energy of the filtered signal, and subtract a clean flow cell baseline energy from the determined energy of the filtered signal, to determine a level of contamination in the flow cell. In certain aspects, counting the number of particle events includes extracting raw data of a fixed time interval from an analog to digital converter, determining a DC offset, and replacing the raw data that is below a fixed threshold with zeroes. According to certain embodiments, the threshold is from 1% to 5% of full dynamic range, or the threshold is $1/e^2$ of peak amplitude. In certain aspects, the expected power spectrum variance is based on the pressure of the sheath fluid. According to certain embodiments, the particles are cells. For example, the cells may be cells of a blood sample.

Also provided by the present disclosure are systems (e.g., flow cytometry systems, which may be a subsystem of an automated hematology system) adapted to perform any of the methods of the present disclosure. Such systems may include any of the above-described non-transitory computer-readable media.

Figure 25:
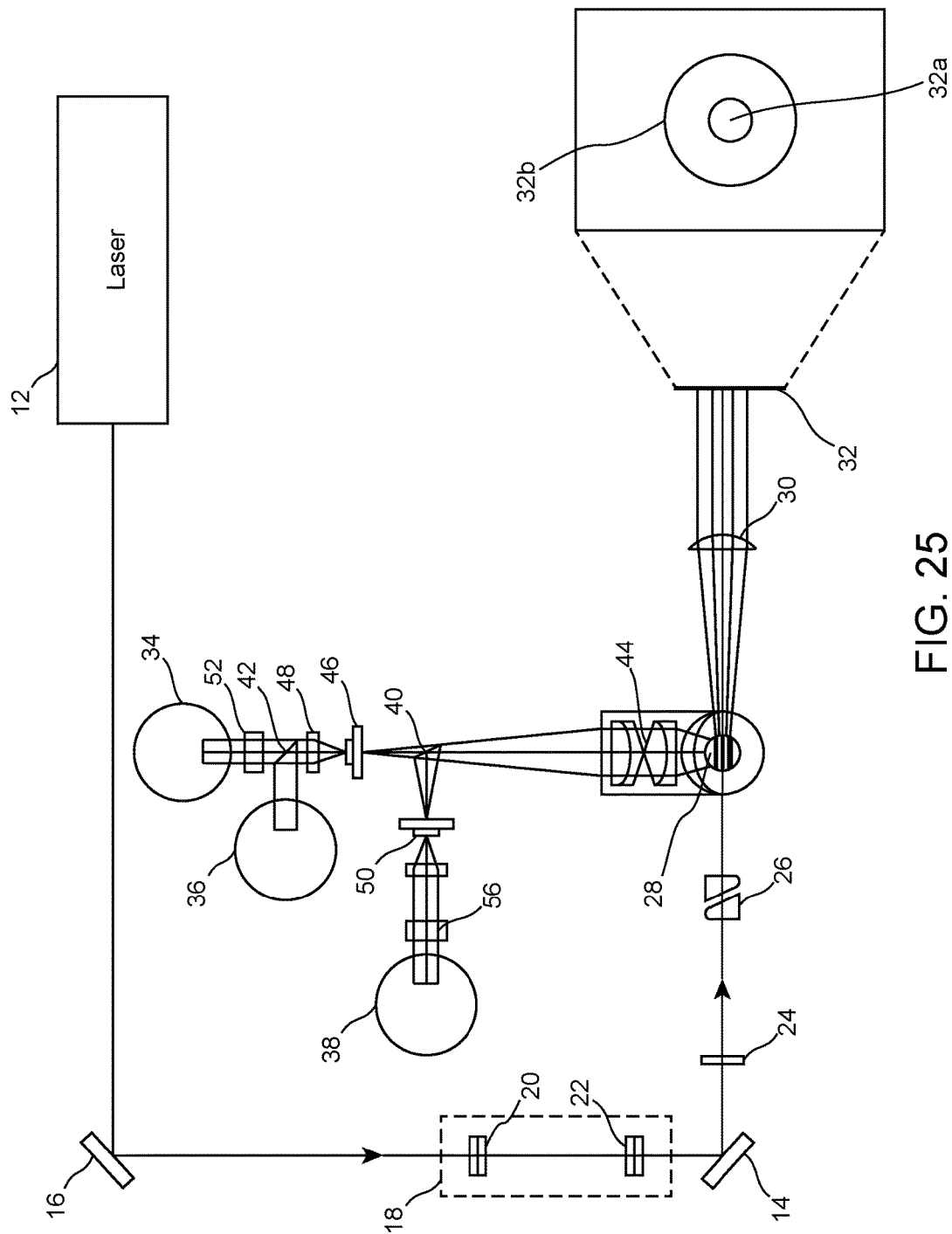
FIG. 25 is a schematic illustration of an example flow cytometer according to one embodiment which finds use in implementing the methods of the present disclosure.

In certain aspects, a system of the present disclosure is a flow cytometer. Such a system includes a flow cell, an excitation source positioned to excite particles of a sample of interest (e.g., a blood sample) flowing through the flow cell, and one or more detectors for detecting optical signals emitted from the excited particles. An example of a flow cytometer which may include any of the above-described non-transitory computer-readable media and suitable for practicing the methods of the present disclosure is schematically illustrated in FIG. 25. Flow cytometer 10 includes a source of light 12, a front mirror 14 and a rear mirror 16 for beam bending, a beam expander module 18 containing a first cylindrical lens 20 and a second cylindrical lens 22, a focusing lens 24, a fine beam adjuster 26, a flow cell 28, a forward scatter lens 30, a bulls-eye detector 32, a first photomultiplier tube 34, a second photomultiplier tube 36, and a third photomultiplier tube 38. The bulls-eye detector 32 has an inner detector 32a for 0° light scatter and an outer detector 32b for 7° light scatter.

In certain aspects, the source of light is a laser. However, other sources of light can be used, such as, for example, lamps (e.g., mercury, xenon). The source of light 12 can be a vertically polarized air-cooled Coherent Cube laser, commercially available from Coherent, Inc., Santa Clara, Calif. Lasers having wavelengths ranging from 350 nm to 700 nm can be used. Operating conditions for the laser are substantially similar to those of lasers currently used with "CELL-DYN" automated hematology analyzers.

Additional details relating to the flow cell, the lenses, the focusing lens, the fine-beam adjust mechanism and the laser focusing lens can be found in U.S. Pat. No. 5,631,165, incorporated herein by reference, particularly at column 41, line 32 through column 43, line 11. The forward optical path system shown in FIG. 2 includes a spherical plano-convex lens 30 and a two-element photo-diode detector 32 located in the back focal plane of the lens. In this configuration, each point within the two-element photodiode detector 32 maps to a specific collection angle of light from cells moving through the flow cell 28. The detector 32 can be a bulls-eye detector capable of detecting axial light loss (ALL) and intermediate angle forward scatter (IAS). U.S. Pat. No. 5,631,165 describes various alternatives to this detector at column 43, lines 12-52.

A first photomultiplier tube 34 (PMT1) measures depolarized side scatter (DSS). The second photomultiplier tube 36 (PMT2) measures polarized side scatter (PSS), and the third photomultiplier tube 38 (PMT3) measures fluorescence emission from 440 nm to 680 nm, depending upon the fluorescent dye selected and the source of light employed. The photomultiplier tube collects fluorescent signals in a broad range of wavelengths in order to increase the strength of the signal. Side-scatter and fluorescent emissions are directed to these photomultiplier tubes by dichroic beam splitters 40 and 42, which transmit and reflect efficiently at the required wavelengths to enable efficient detection. U.S. Pat. No. 5,631,165 describes various additional details relating to the photomultiplier tubes at column 43, line 53 though column 44, line 4.

Sensitivity is enhanced at photomultiplier tubes 34, 36, and 38, when measuring fluorescence, by using an immersion collection system. The immersion collection system is one that optically couples the first lens 30 to the flow cell 28 by means of a refractive index matching layer, enabling collection of light over a wide angle. U.S. Pat. No. 5,631,165 describes various additional details of this optical system at column 44, lines 5-31.

The condenser 44 is an optical lens system with aberration correction sufficient for diffraction limited imaging used in high resolution microscopy. U.S. Pat. No. 5,631,165 describes various additional details of this optical system at column 44, lines 32-60.

The functions of other components shown in FIG. 25, i.e., a slit 46, a field lens 48, and a second slit 50, are described in U.S. Pat. No. 5,631,165, at column 44, line 63 through column 45, line 26. Optical filters 52 or 56 and a polarizer 52 or 56, which are inserted into the light paths of the photomultiplier tubes to change the wavelength or the polarization or both the wavelength and the polarization of the detected light, are also described in U.S. Pat. No. 5,631,165, at column 44, line 63 through column 45, line 26. Optical filters that are suitable for use herein include bandpass filters and long-pass filters.

The photomultiplier tubes 34, 36, and 38 detect either side-scatter (light scattered in a cone whose axis is approximately perpendicular to the incident laser beam) or fluorescence (light emitted from the cells at a different wavelength from that of the incident laser beam).

While select portions of U.S. Pat. No. 5,631,165 are referenced above, U.S. Pat. No. 5,631,165 is incorporated herein by reference in its entirety. According to certain embodiments, a flow cytometer of the present disclosure employs an Avalanche Photodiode (APD) as the photosensor.

The following examples are offered by way of illustration and not by way of limitation.

EXPERIMENTAL

Example 1: Removal of Undesirable Cell Event Signals for Event Detection

In this example of event detection, the particles are cells, and undesirable cell event signals are removed to obtain a clean platelet (PLT) cell histogram.

Figure 4:
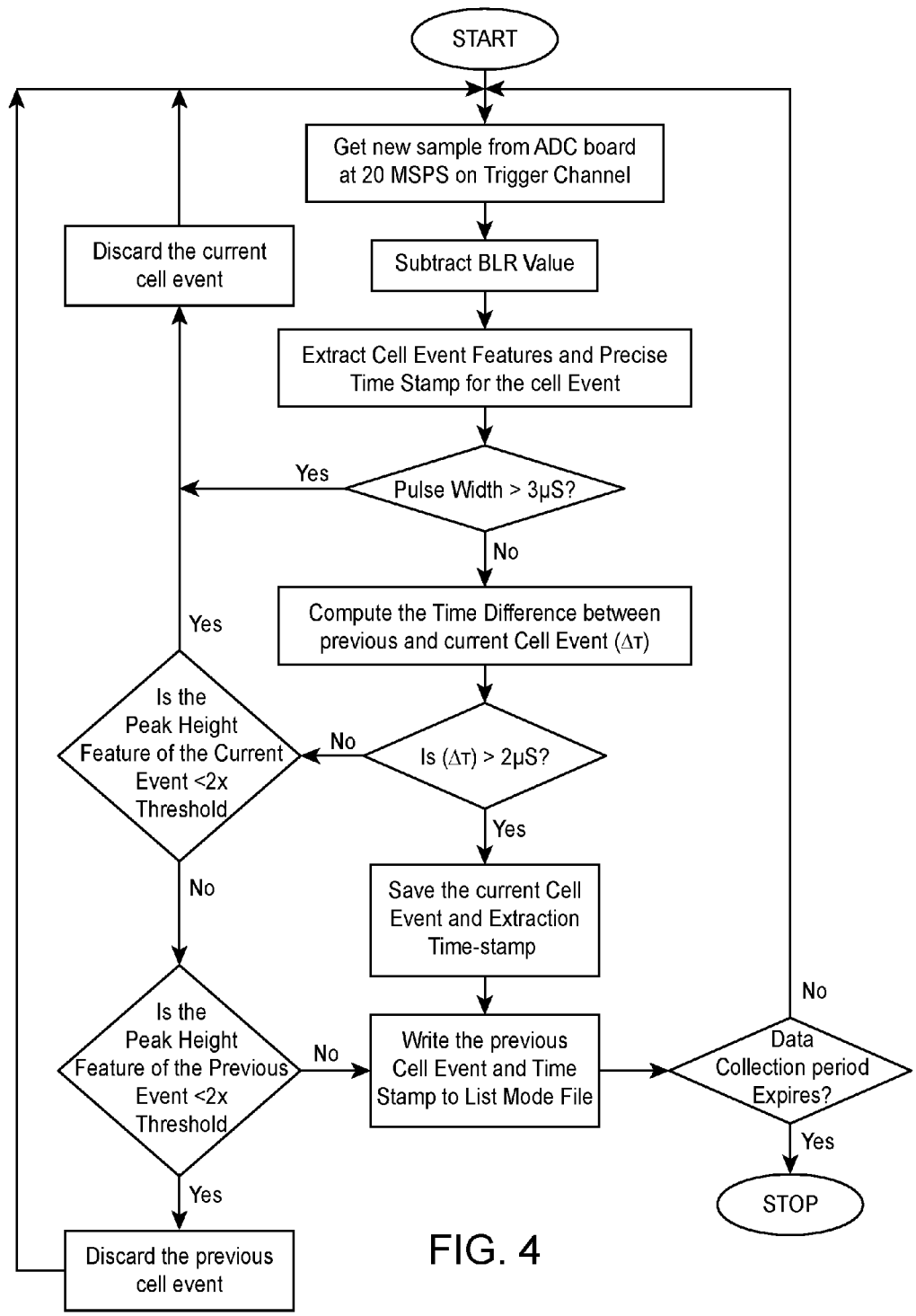
FIG. 4 is a flowchart for removing invalid cell event signals according to one embodiment of the present disclosure.

A flow chart for the method used in this example is shown in FIG. 4. Samples are acquired from an analog to digital converter (ADC) at 20 million samples per second resolution on the trigger channel. Following sample acquisition and subtraction of the baseline restore (BLR) value, cell event features are extracted and time-stamped. If the pulse width is greater than 3 µs, the current cell event is discarded. If the pulse width is less than 3 µs, the time difference between the previous and current event is computed. If the time difference between the previous and current cell event is greater than 2 µs, the current event is saved and the time-stamp extracted. If the peak height feature of the current event is less than 2× the threshold, the current event is discarded. If the peak height feature of the current event is not less than 2× the threshold and the peak height feature of the previous event is less than 2× the threshold, the previous event is discarded. If the peak height feature of the current event is not less than 2× the threshold and the peak height feature of the previous event is not less than 2× the threshold, the previous event and time-stamp are written to a list mode file. The above process is carried out until the data collection period expires.

Figure 5:
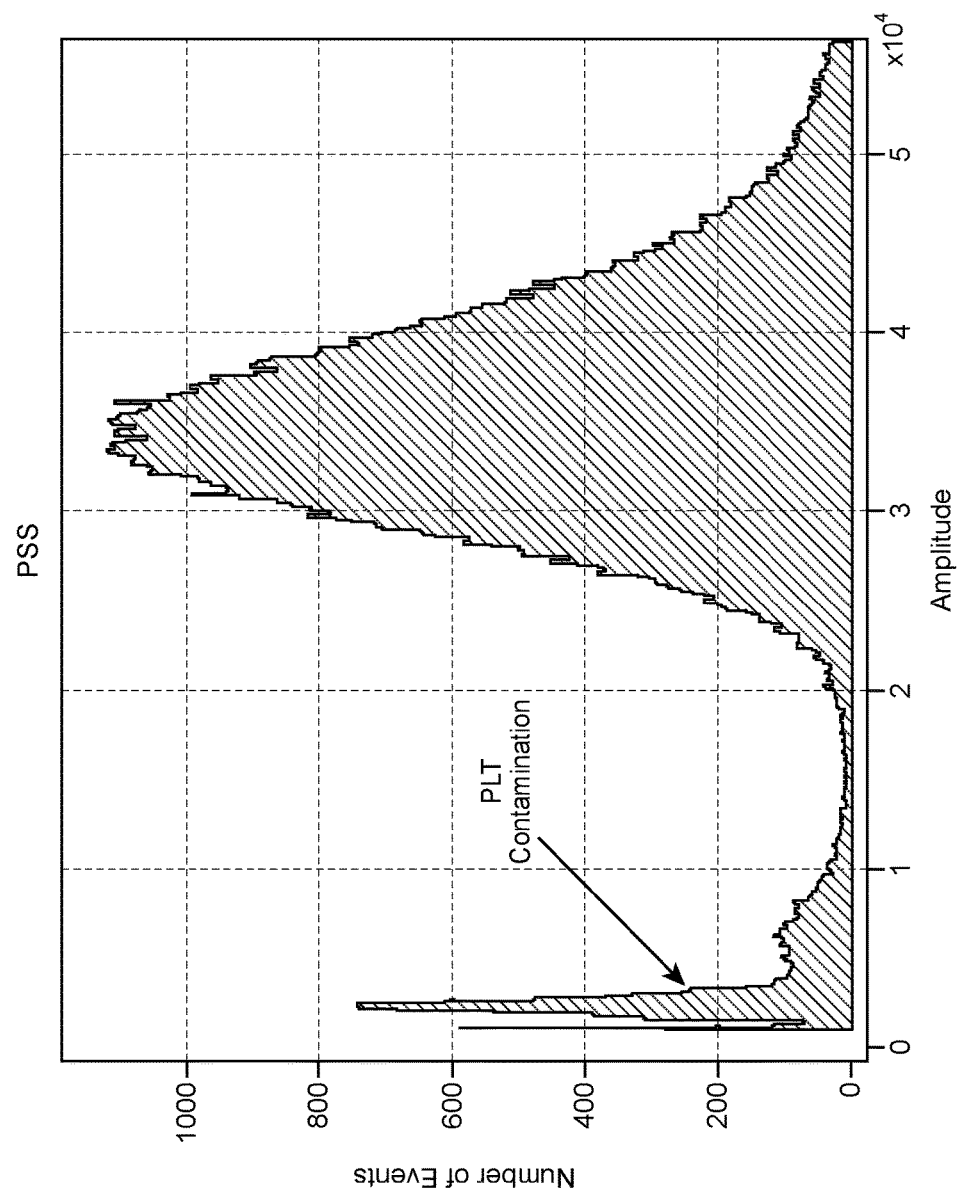
FIG. 5 depicts a plot showing contamination of platelet count and concentration by artifacts.
Figure 6:
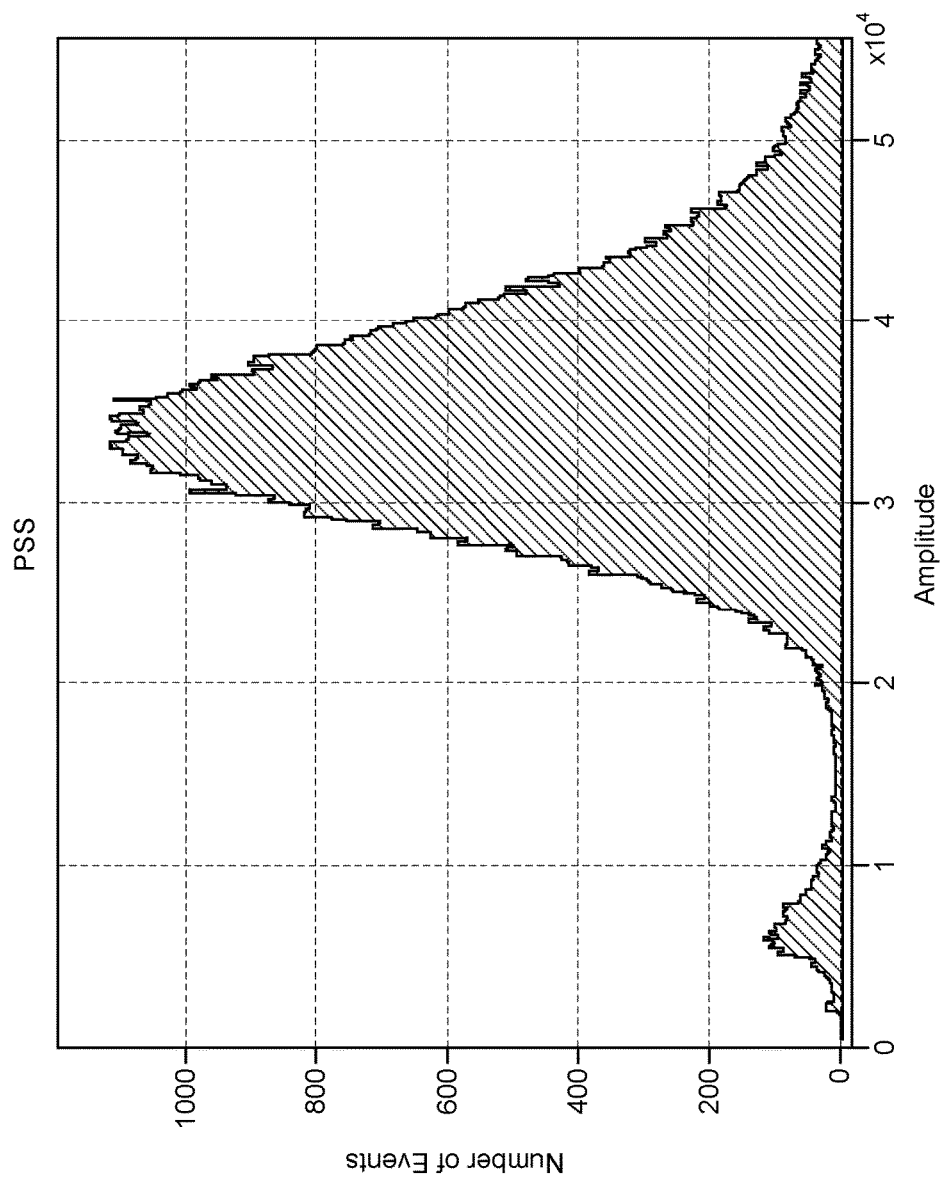
FIG. 6 depicts a plot showing the elimination of undesirable events, as achieved using a method according to one embodiment of the present disclosure.
Figure 7:
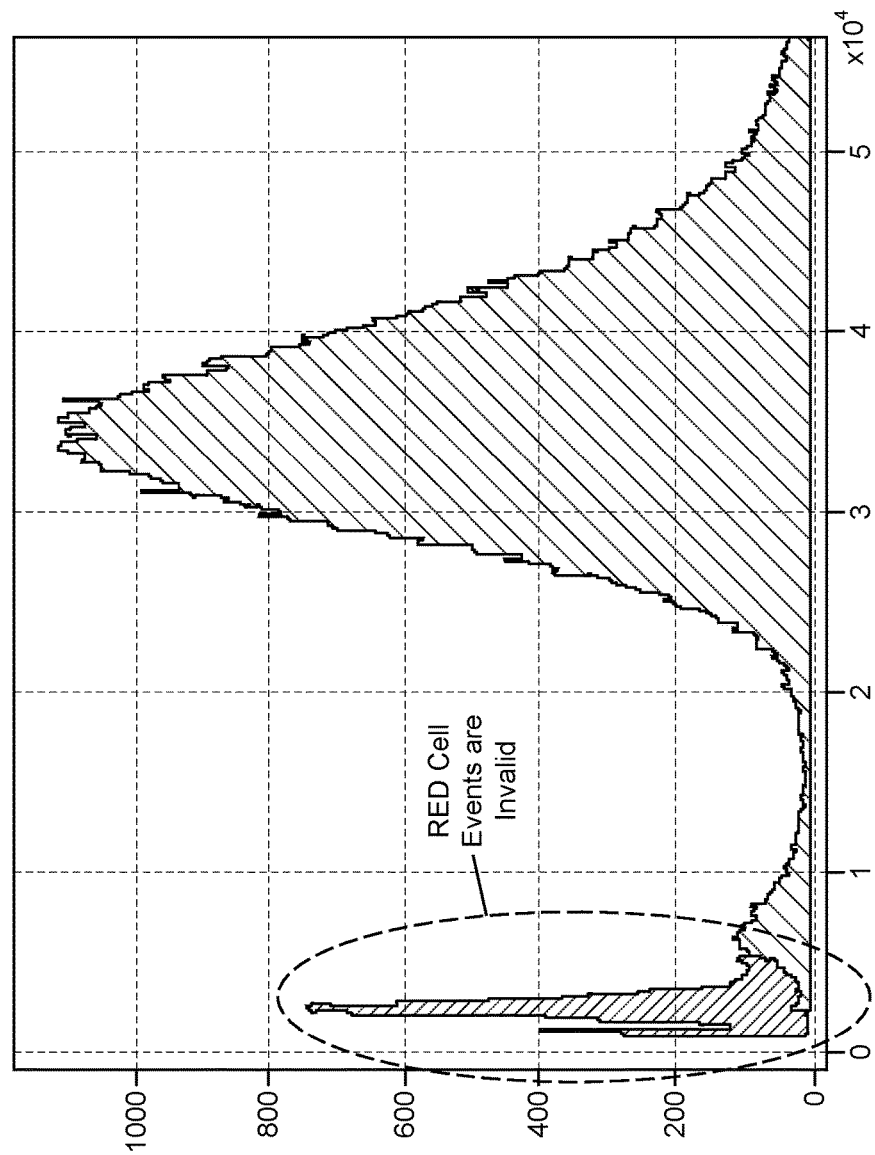
FIG. 7 depicts a plot showing RBC and PLT events.
Figure 8:
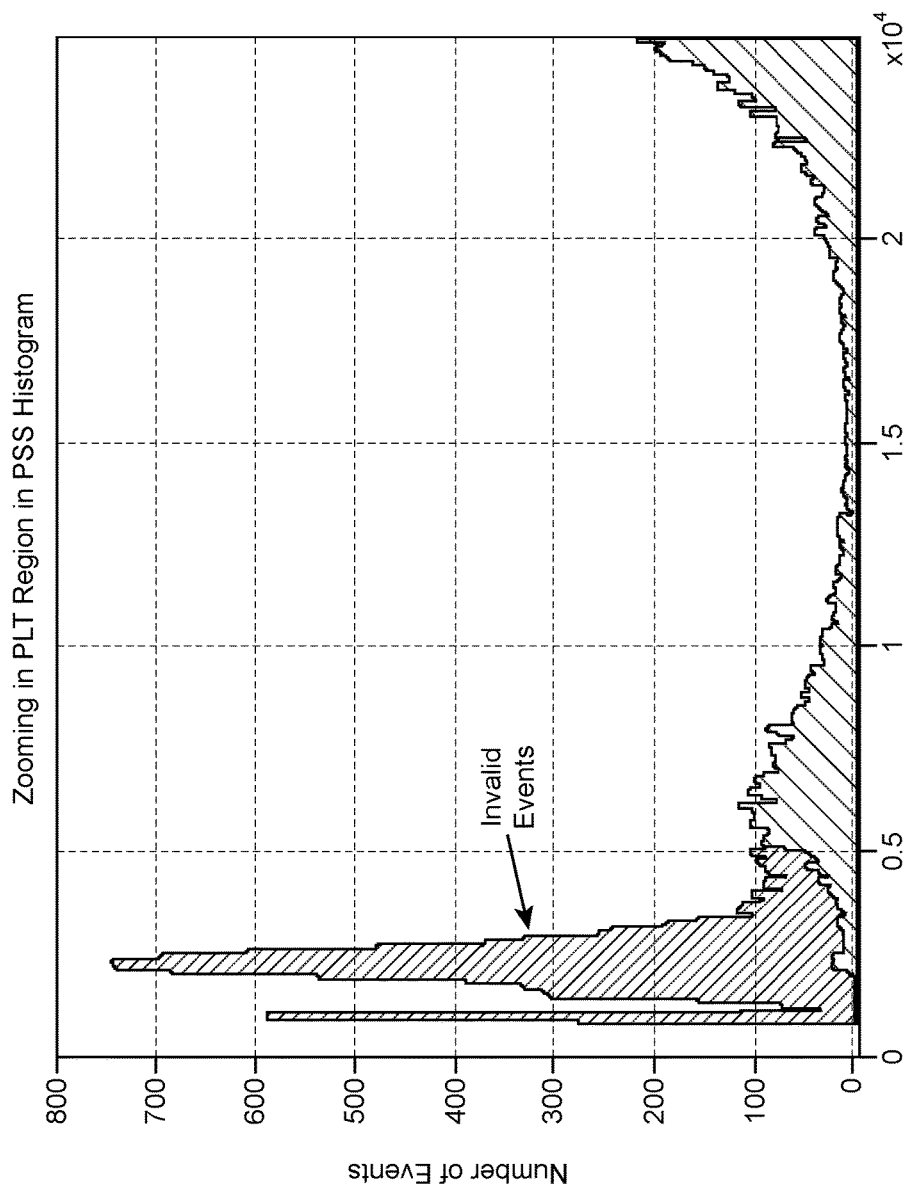
FIG. 8 depicts a zoomed-in section of the plot in FIG. 7.

The utility of this example method for obtaining clean platelet (PLT) cell histograms is demonstrated in FIGS. 5-8. FIG. 5 shows the contamination of the PLT population at closer to the origin on the Amplitude axis. FIG. 7 shows the contamination of the PLT population very clearly in the PSS side scattered channel. In FIG. 7, invalid events are shown clearly in different color. Those events are not PLT cell events but invalid events generated by optical artifact, APD thermal effect, Fluidics drift or Electronics baseline noise. FIG. 6 is the output of this algorithm to achieve clean log normal distribution of the PLT cell population. In this example, the sample was diluted by 1:250 and the injection rate was 2.9 µL/s.

Example 2: Improved Capture of Cell Events by Dynamic Adjustment of Optical Gains In this example, a digital data capture subsystem keeps track of cell event counts as well as the duration of the assay. At a predetermined time in the assay, if the data capture system determines that certain cell event signals (e.g., forward and scatter light from the cell events) are below an expected value, the variable gain settings of the photo electronics signals are increased. If the data capture subsystem finds many saturated cell events compared to unsaturated events in the fixed amount of time (~300 ms) at the beginning of an assay, the variable gain settings of the photo electronics signals are decreased.

Figure 10:
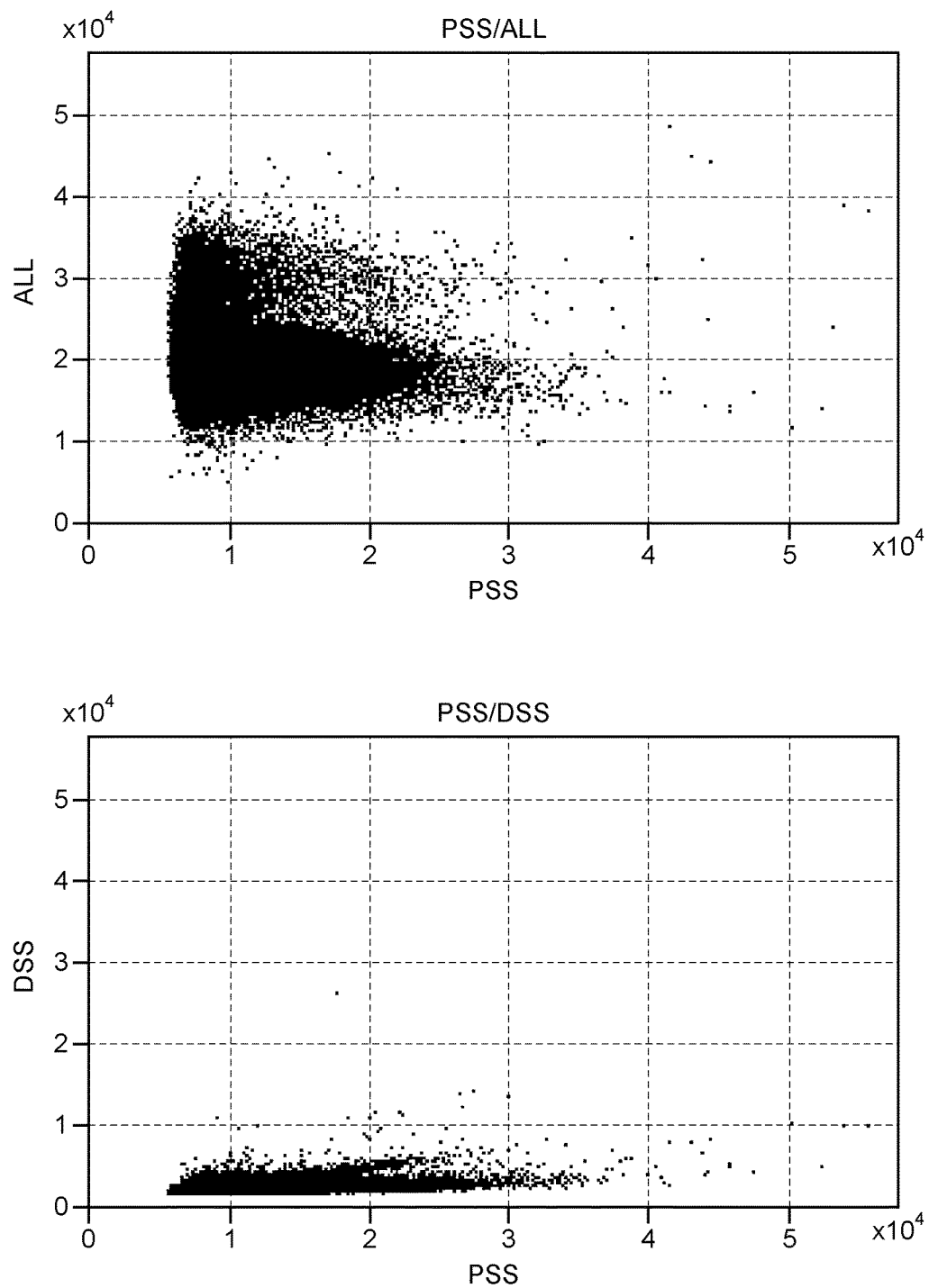
FIG. 10 depicts plots that show counts performed under a fixed gain setting during the entire assay.
Figure 11:
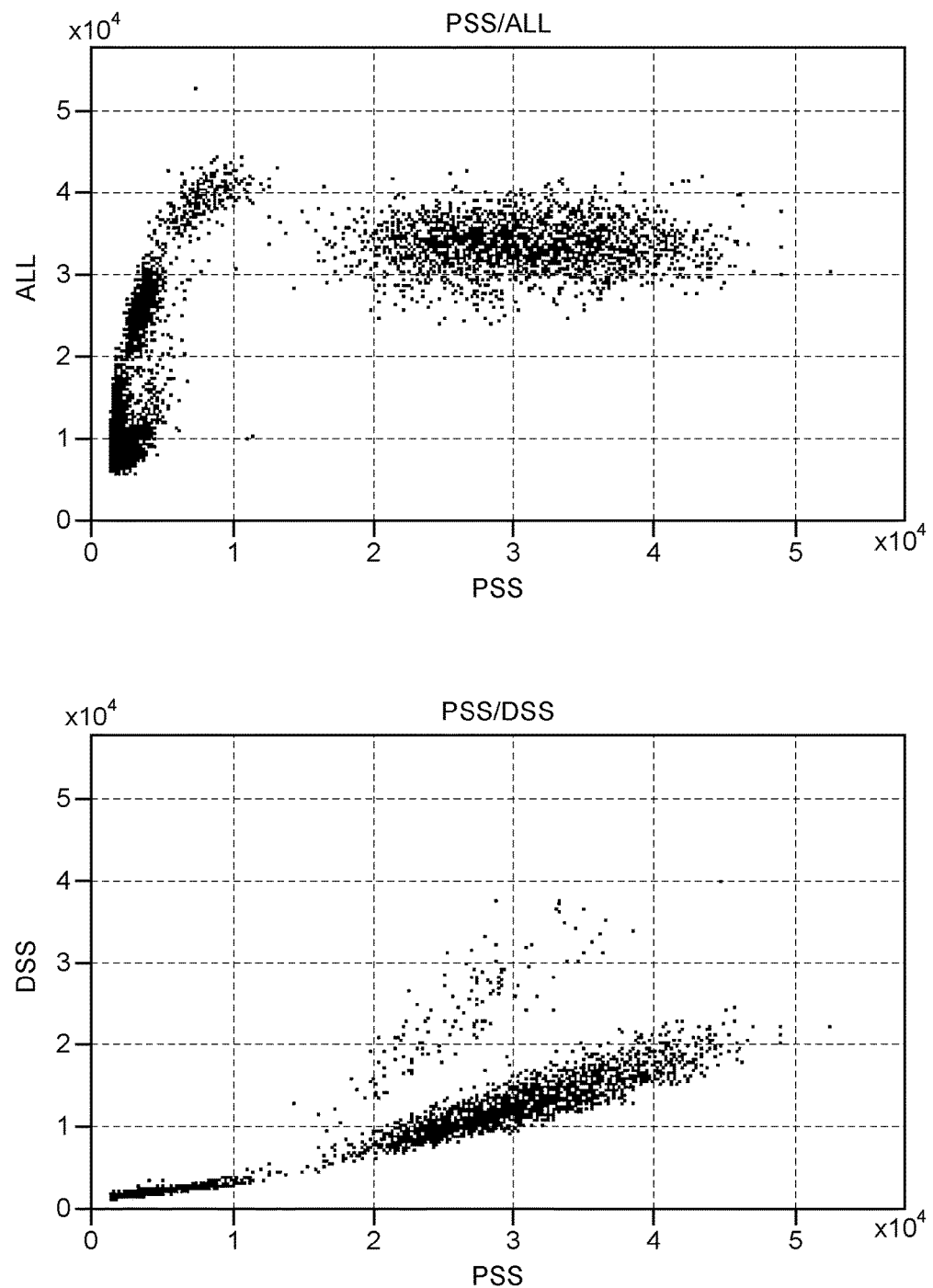
FIG. 11 depicts plots that show counts performed with dynamic gain adjustment during the assay.

Plots of cell events in the absence of dynamic gain adjustment are shown in FIG. 10. Plots of cell events in which dynamic gain adjustment was employed during the assay are shown in FIG. 11. In FIGS. 10 and 11, the upper and lower plots are PSS/ALL and PSS/DSS, respectively.

FIGS. 10 and 11 demonstrate the beneficial effect of dynamic gain adjustment, especially in body fluid mode or any assay where the dye amount for the assay is fixed based on the average cell count expectation. This method addresses the problem of dye penetration variation in the nucleus of the cells, especially when there is significantly more or less amount of nucleated cells in the assay than expected. FIG. 10 shows the effect when there are more cells than expected in the assay. Since all the cells are not stained, it is very hard to differentiate the cell population as the cluster distance between the cell population is very small. FIG. 11 shows that the method described here involving variable gain adjustment facilitates separating the cell population clusters in the scatter plot. FIG. 11 shows where the nucleated cells are more than expected and the fixed amount of dye was insufficient to stain all the nucleated cells. Conversely, when there are much fewer nucleated cells than expected, the fixed amount of dye stains the nucleus and plasma and in turn, saturates the cell event response on the photo sensors. Saturated signals do not carry any additional information for cluster separation and hence it is very desirable to reduce the gain dynamically while the assay is active.

An additional advantage of this method is to separate one assay in two or more pre-determined gain settings. FIG. 9 shows the RBC assay is divided into two groups to achieve better extraction of features of the PLT cell population. It shows that small cell events can be extracted at larger gain settings and larger cells can be extracted at lesser gain settings. This way it is possible to take advantage of complete dynamic range of the analog to digital converter electronics.

The decision can be made dynamically and during the assay runtime and gain can be adjusted and stabilized within tens of milliseconds without affecting data integrity.

Figure 13:
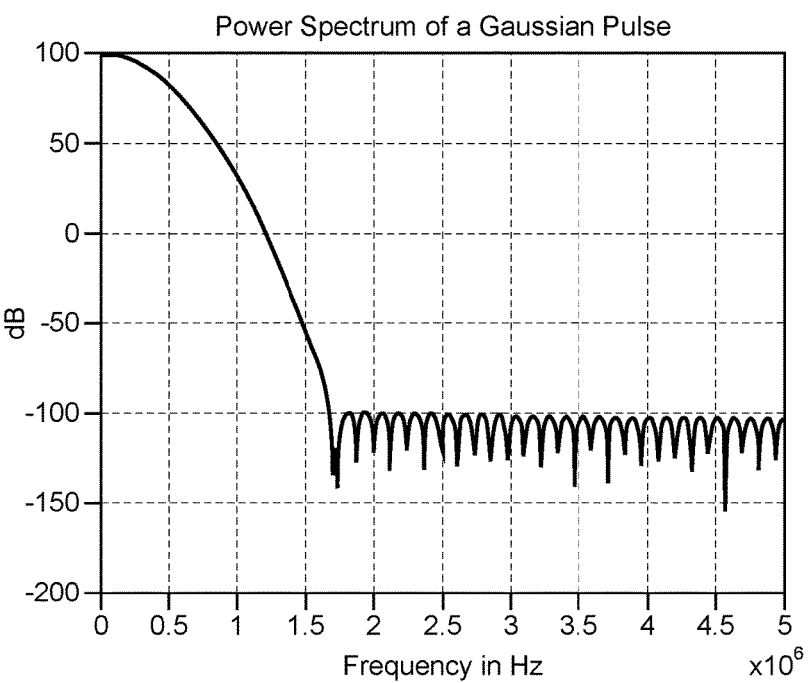
FIG. 13 depicts the power spectrum of the ideal Gaussian pulse.
Figure 14:
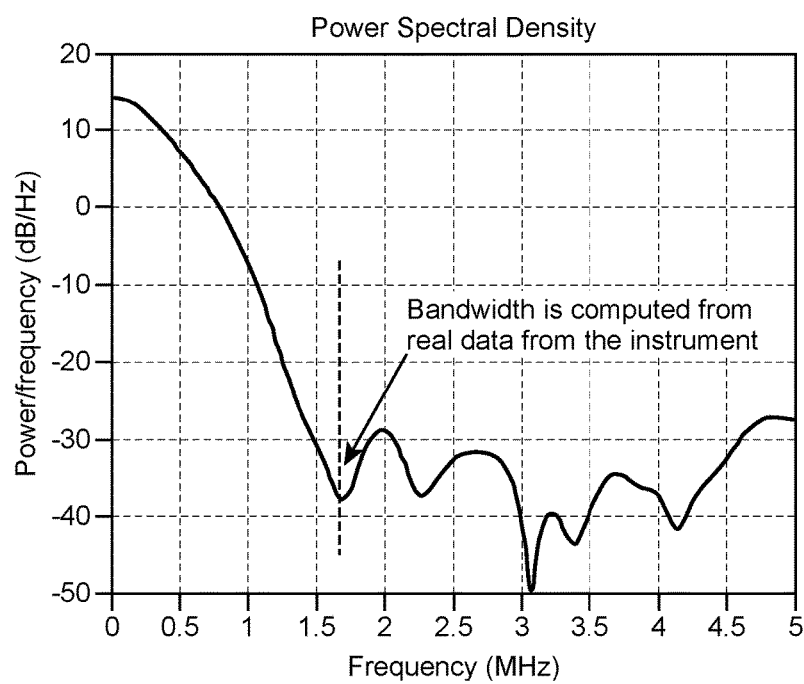
FIG. 14 depicts the power spectrum obtained from a flow cytometer.

Example 3: Detection of Early-Stage Flow Cell Contamination by Analyzing Cell Event Responses in the Frequency Domain and the Energy of the High Frequency Component The theoretically ideal Gaussian pulse of 2 microsecond duration at 10 MSPS occupies 1.75 MHz bandwidth. Instead of using the theoretical value, the bandwidth was computed from experimental data taken on a clean flow cell with existing electronics. Experimental data shows that the interested bandwidth in the clean flow cell is approximately 1.65 MHz and is therefore very close to the theoretical one. The power spectrum of the ideal Gaussian pulse and the power spectrum of experimental data taken from a clean flow cell are shown in FIGS. 13 and 14, respectively.

A Gaussian pulse represents a clean cell event signal. Contamination in the flow cell adds more energy in the cell event signal. The inverse response of the Gaussian spectrum is computed in the frequency domain to subtract the energy of the cell event that represents the clean flow cell. The remaining energy in the cell event is directly proportional to the contamination in the flow cell. Effective normalization of the spectrum depends on the system noise floor. When the noise floor is sufficiently low (e.g., less than 1% of the full dynamic range), the power spectrum may be readily normalized to the cell amplitude.

Figure 15:
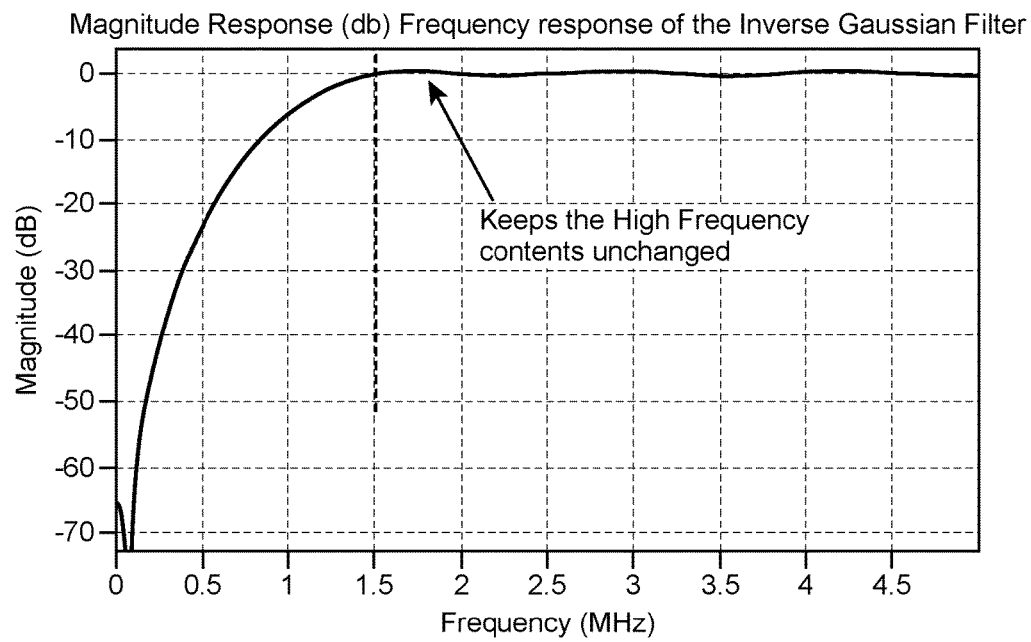
FIG. 15 depicts the frequency response of an inverse Gaussian filter.

From the raw data, the number of cell events is counted based on the gated peaks. Once the peaks are identified, the raw data is first floored to threshold value to eliminate baseline noise. Then raw data of only cell events is filtered with the inverse Gaussian filter. A graph of the frequency response of the inverse Gaussian filter is depicted in FIG. 15.

Output of the inverse Gaussian filter indicates any energy from flow cell contamination. In order to precisely measure the impact of the contamination, residual energy for clean flow cell events are subtracted. The final value is an excellent indication of remaining energy due to multiple reflections from the flow cell.

Figure 16:
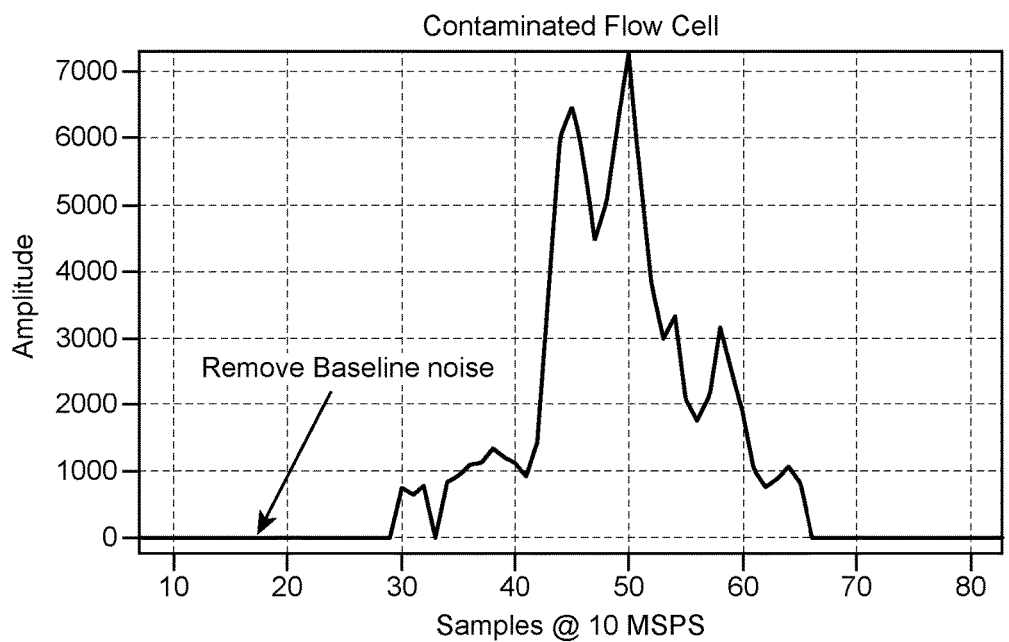
FIG. 16 depicts the time-domain signal for a highly-contaminated flow cell, in which baseline noise was removed from the raw data from an ADC.
Figure 17:
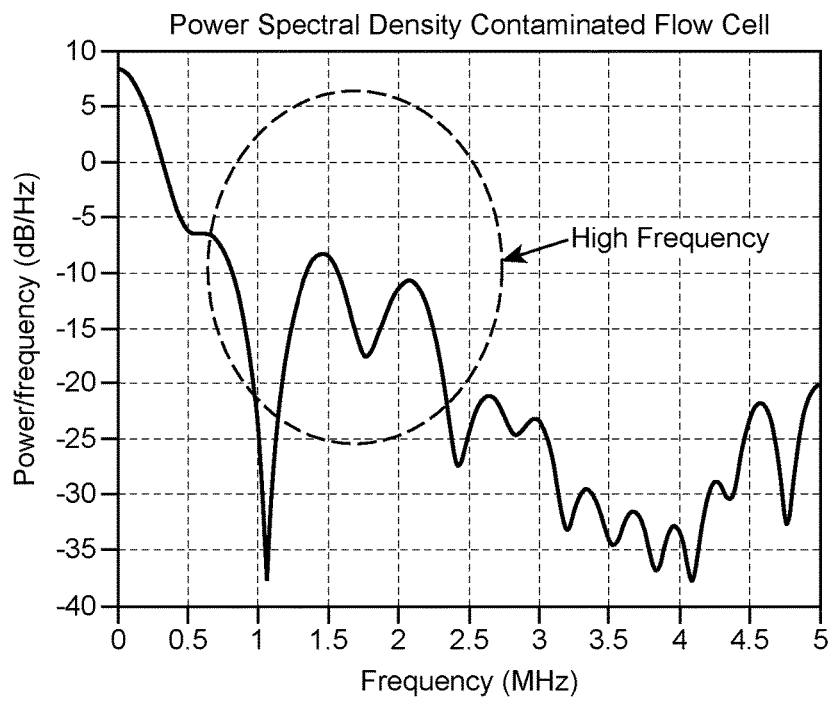
FIG. 17 depicts the frequency domain characteristic of the highly-contaminated flow cell (power spectrum of the raw data).
Figure 18:
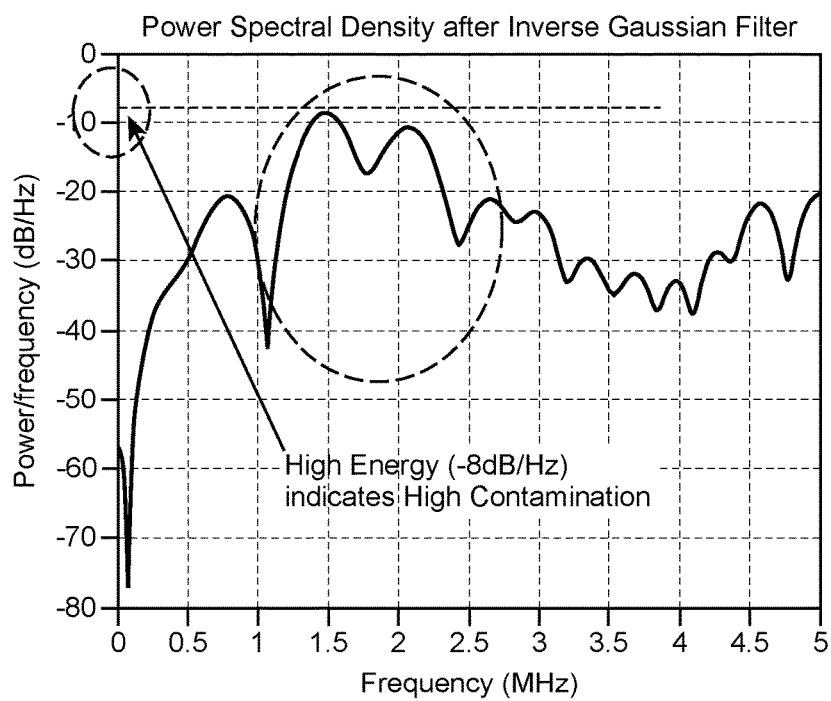
FIG. 18 depicts the power spectrum of the raw data after removing the energy equivalent to a clean flow cell from the raw data of the highly-contaminated flow cell.

Data obtained from a highly-contaminated flow cell is shown in FIGS. 16-18. FIG. 16 shows the time-domain signal for a highly-contaminated flow cell, in which baseline noise was removed from the raw data from an ADC (stage 1). FIG. 17 shows the frequency domain characteristic of the highly-contaminated flow cell (power spectrum of the raw data) (stage 2). FIG. 18 shows the power spectrum of the raw data after removing the energy equivalent to a clean flow cell. In this example, the high energy (−8 dB/Hz) indicates a high level of contamination.

Figure 19:
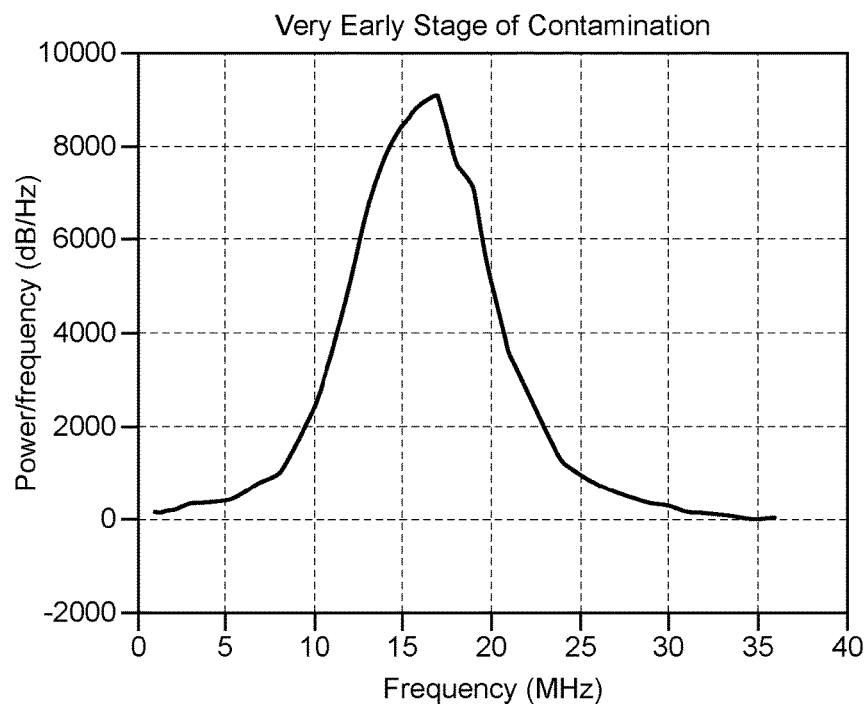
FIG. 19 depicts the time-domain signal for a flow cell at an early stage of contamination, in which baseline noise was removed from the raw data from an ADC.
Figure 20:
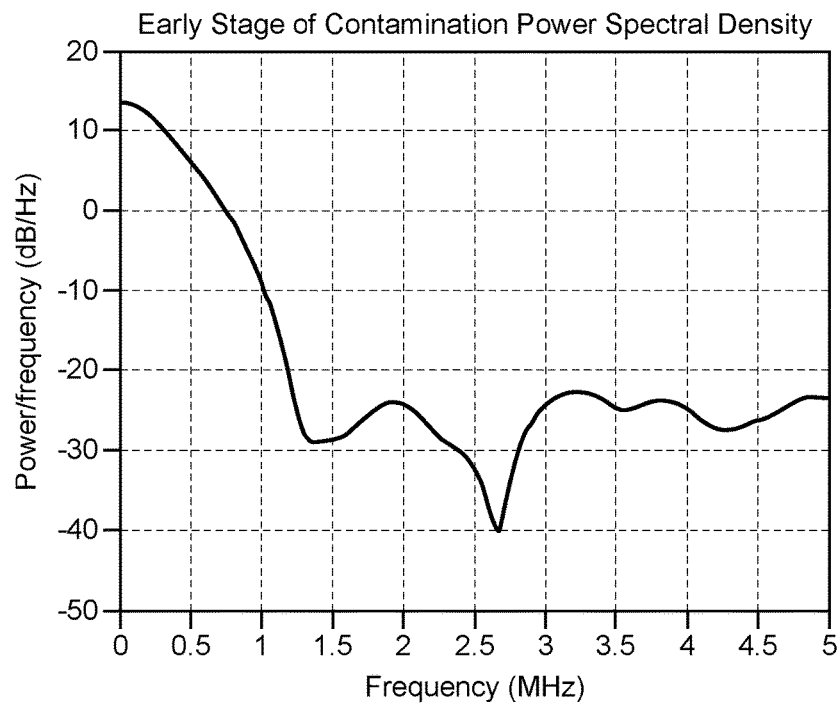
FIG. 20 depicts the frequency domain characteristic of the flow cell at an early stage of contamination (power spectrum of the raw data).
Figure 21:
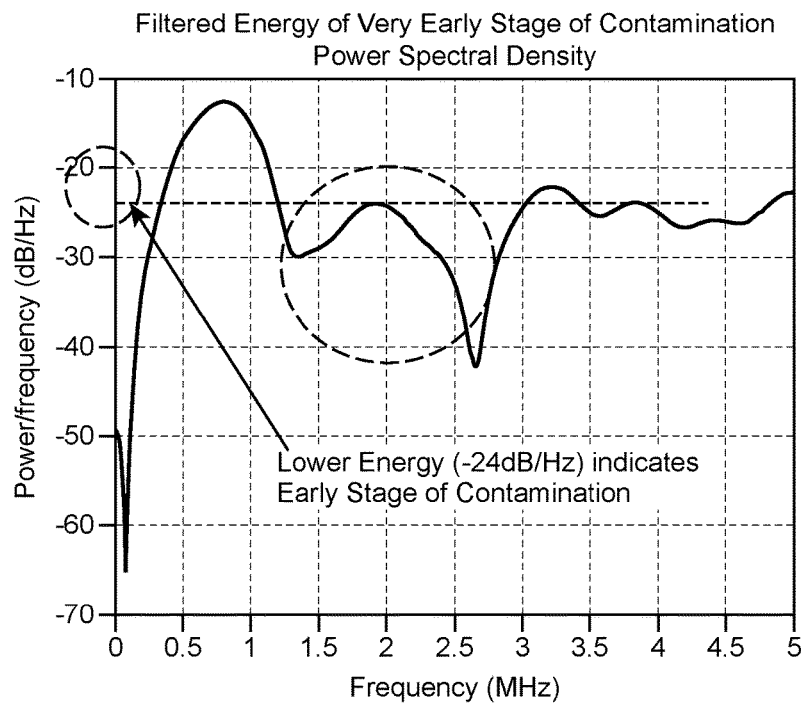
FIG. 21 depicts the power spectrum of the raw data after removing the energy equivalent to a clean flow cell from the raw data of the flow cell at an early stage of contamination.

Data obtained from a flow cell at an early stage of contamination is shown in FIGS. 19-21. FIG. 19 shows the time-domain signal for a flow cell at an early stage of contamination, in which baseline noise was removed from the raw data from an ADC. FIG. 20 shows the frequency domain characteristic of the flow cell at an early stage of contamination (power spectrum of the raw data). FIG. 21 shows the power spectrum of the raw data after removing the energy equivalent to a clean flow cell. In this example, the lower energy (−24 dB/Hz) indicates an early stage of contamination.

Figure 22:
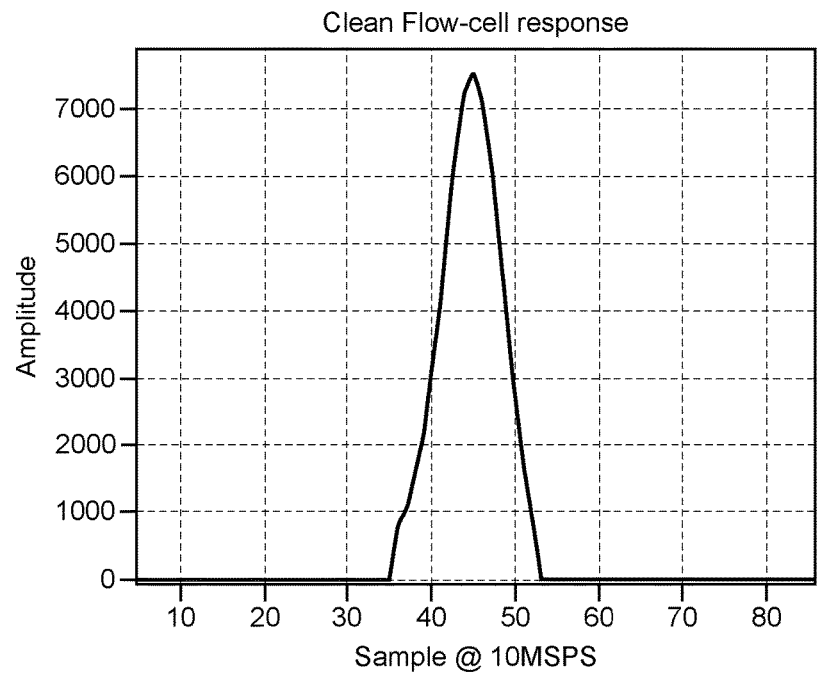
FIG. 22 depicts the time-domain signal for a flow cell that is not contaminated, in which baseline noise was removed from the raw data from an ADC.
Figure 23:
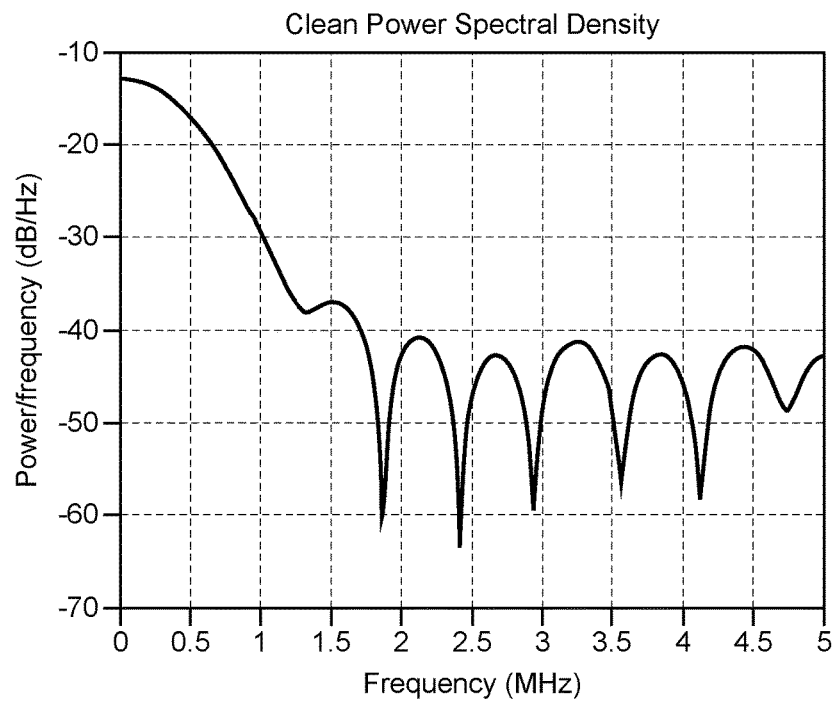
FIG. 23 depicts the frequency domain characteristic of the flow cell that is not contaminated (power spectrum of the raw data).
Figure 24:
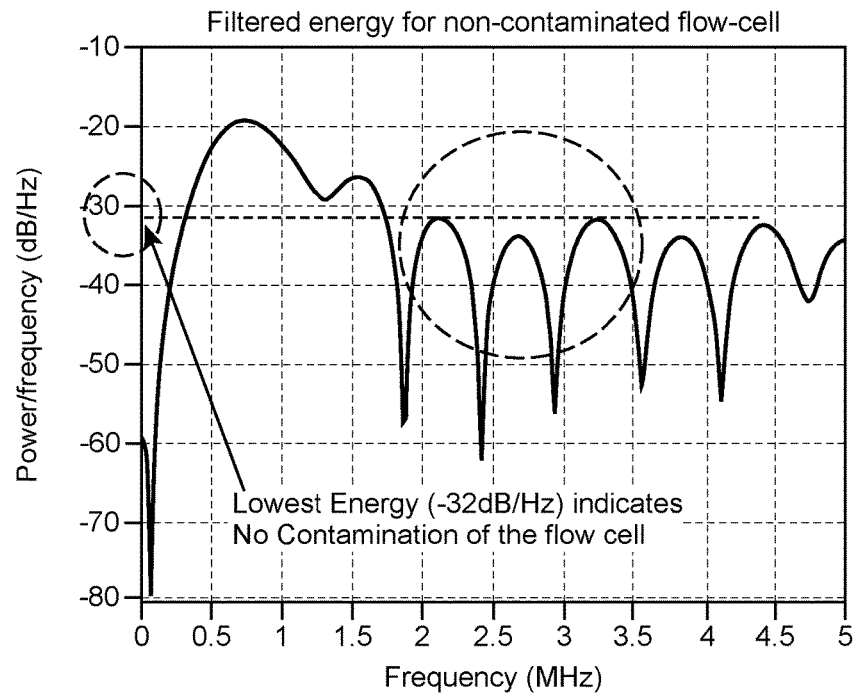
FIG. 24 depicts the power spectrum of the raw data after removing the energy equivalent to a clean flow cell from the raw data of the flow cell that is not contaminated.

Data obtained from a flow cell that is not contaminated is shown in FIGS. 22-24. FIG. 22 shows the time-domain signal for a flow cell that is not contaminated, in which baseline noise was removed from the raw data from an ADC. FIG. 23 shows the frequency domain characteristic of the flow cell that is not contaminated (power spectrum of the raw data). FIG. 24 shows the power spectrum of the raw data after removing the energy equivalent to a clean flow cell. The low energy (−32 dB/Hz) indicates that the flow cell is not contaminated.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for detecting events in a flow cytometer, comprising:
flowing particles through a flow cell of the flow cytometer;
optically interrogating the particles flowing through the flow cell;
extracting putative event features;
time-stamping putative events;
determining a time difference between a putative previous event and a putative current event;
comparing the time difference to a threshold duration, wherein:
if the time difference is greater than the threshold duration, storing the putative current event as a current event; and
if the time difference is less than the threshold duration, comparing a peak height feature of the putative current event and a peak height feature of the putative previous event to a threshold peak height, wherein:
if the peak height feature of the putative current event is less than the threshold peak height, discarding the putative current event; and
if the peak height feature of the putative previous event is greater than the threshold peak height, storing the putative previous event as a previous event.

2. The method according to claim 1, wherein an event is distinguished from a signal selected from the group consisting of: optical system side-lobes, fluidics drift, baseline drift, flow cell contamination, and combinations thereof.

3. The method according to claim 1, wherein flowing particles through the flow cell comprises flowing the particles at a sheath pressure of 9 psi or greater.

4. The method according to claim 1, wherein comparing a peak height feature of the putative current event and a peak height feature of the putative previous event to a threshold peak height comprises determining whether the peak heights of the putative current event and putative previous event are less than 2× a threshold peak height.

5. The method according to claim 1, wherein the threshold duration is 2.5 µs or less.

6. The method according to claim 1, wherein optically interrogating the particles comprises exciting the cells using a laser.

7. The method according to claim 1, wherein the particles are cells and an event is a cell event.

8. The method according to claim 5, wherein the threshold duration is 2 µs.

9. The method according to claim 6, wherein the beam height of the laser is 5 µm or greater.

10. The method according to claim 9, wherein the beam height of the laser is 8 µm.

11. The method according to claim 7, wherein the cells are from a blood sample.

12. The method according to claim 11, wherein the cell event is a small cell event.

13. The method according to claim 12, wherein the small cell event is a platelet event.

14. The method according to claim 12, wherein the small cell event is a microorganism cell event or a cell debris event.

* * * * *